United States Patent
Komatsu et al.

(10) Patent No.: US 10,746,719 B2
(45) Date of Patent: Aug. 18, 2020

(54) SOIL ANALYZING DEVICE AND SOIL ANALYZING METHOD

(71) Applicants: Komatsu Seiki Kosakusho Co., Ltd., Suwa-shi, Nagano (JP); National University Corporation Shinshu University, Matsumoto-shi, Nagano (JP)

(72) Inventors: Takafumi Komatsu, Suwa (JP); Tsunaki Misawa, Suwa (JP); Naoto Inoue, Kamiina-gun (JP); Eishi Momosaki, Kamiina-gun (JP); Koji Orii, Kamiina-gun (JP)

(73) Assignees: KOMATSU SEIKI KOSAKUSHO CO., LTD, Suwa-shi (JP); NATIONAL UNIVERSITY CORPORATION SHINSHU UNIVERSITY, Matsumoto-shi (JP)

( * ) Notice: Subject to any disclaimer, the term of this patent is extended or adjusted under 35 U.S.C. 154(b) by 0 days.

(21) Appl. No.: 16/309,486

(22) PCT Filed: Jun. 19, 2017

(86) PCT No.: PCT/JP2017/022568
§ 371 (c)(1),
(2) Date: Dec. 13, 2018

(87) PCT Pub. No.: WO2017/221901
PCT Pub. Date: Dec. 28, 2017

(65) Prior Publication Data
US 2019/0310238 A1    Oct. 10, 2019

(30) Foreign Application Priority Data
Jun. 20, 2016  (JP) .................................. 2016-121860

(51) Int. Cl.
*G01N 33/24* (2006.01)
*G01N 21/64* (2006.01)
*G01N 27/72* (2006.01)

(52) U.S. Cl.
CPC ............. *G01N 33/24* (2013.01); *G01N 21/64* (2013.01); *G01N 27/72* (2013.01); *G01N 2033/245* (2013.01)

(58) Field of Classification Search
None
See application file for complete search history.

(56) References Cited

U.S. PATENT DOCUMENTS

2004/0145379 A1   7/2004  Buss
2015/0123666 A1   5/2015  Leppanen et al.
(Continued)

FOREIGN PATENT DOCUMENTS

JP    2015-516086 A    6/2015
JP    2015-169644 A    9/2015
JP        5885168 B2   3/2016

OTHER PUBLICATIONS

Chen et al., "Chemical and physical properties of rhizosphere and bulk soils of three tea plants cultivated in Ultisols", Geoderma, 2006, 136, pp. 378-387, cited in ISR (10 pages).
(Continued)

*Primary Examiner* — Paresh Patel
(74) *Attorney, Agent, or Firm* — Westerman, Hattori, Daniels & Adrian, LLP

(57) ABSTRACT

A soil analyzing device includes: a sensor having an excitation coil and a detection coil; a measurement unit that generates an excitation signal to be input to the excitation coil, and processes a detection signal output from the detection coil; a storage unit that stores data concerning the correlation between a quantitative value of the soil fertility characteristics including CEC of two or more types of the
(Continued)

soil having different components and an estimated value of the soil fertility characteristics including CEC found from the processed detection signal measured by the sensor and the measurement unit; and an estimation unit that estimates the soil fertility characteristics based on the detection signal generated by allowing the sensor to apply the alternating magnetic field to the soil to be analyzed and processed by the measurement unit, and by using the data stored in the storage unit.

11 Claims, 30 Drawing Sheets

(56) References Cited

U.S. PATENT DOCUMENTS

2015/0272017 A1   10/2015  Hedley et al.
2017/0090068 A1*   3/2017  Xiang ................ G01N 33/0098

OTHER PUBLICATIONS

Ulusoy et al., "Prediction of soil cation exchange capacity using visible and near infrared spectroscopy", Biosystems Engineering, Elsevier Ltd., 2016, 152, pp. 79-93, cited in ISR (15 pages).

Milori et al., "Organic Matter Study of Whole Soil Samples Using Laser-Induced Fluorescence Spectroscopy", Soil Science Society of America Journal, 2006, 70, pp. 57-63, cited in ISR (9 pages).

Martins et al., "Soil organic matter humification under different tillage managements evaluated by Laser Induced Fluorescence (LIF) and C/N ratio", Soil & Tillage Research, Elsevier Ltd., 2011, 111, pp. 231-235, cited in ISR (5 pages).

"Standard Soil Analysis/ Measurement Method", the Standard Soil Analysis/Measurement Committee, Hakuyusha Co., Ltd., Nov. 15, 1986, pp. 150-154, with concise explanation of relevance, cited in Specification (7 pages).

International Search Report dated Sep. 19, 2017, issued in counterpart application No. PCT/JP2017/022568 (2 pages).

Triantafilis, John et al, "Field level digital soil mapping of cation exchange capacity using electromagnetic induction and a hierarchical spatial regression model", Soil Research, Vo. 1. 47, No. 7, Nov. 6, 2009, pp. 651-663; Cited in Extended European Search Report dated Feb. 3, 2020. (13 Pages).

Triantafilis, John et al,"Application of a mobile electromagnetic sensing system (MESS) to assess cause and management of soil salinization in an irrigated cotton-growing field", Soil Use and Management, vol. 18, No. 4, Dec. 1, 2002, pp. 330-339; Cited in Extended European Search Report dated Feb. 3, 2020. (10 pages).

Murad, Omar et al, "Obtaining Chemical Properties through Soil Electrical Resistivity", Journal of Civil Engineering Research, vol. 2, No. 6, Dec. 1, 2012, pp. 120-128; Cited in Extended European Search Report dated Feb. 3, 2020. (9 pages).

Extended (Supplementary) European Search Report dated Feb. 3, 2020, issued in counterpart EP Application No. 17815369.8. (11 pages).

* cited by examiner

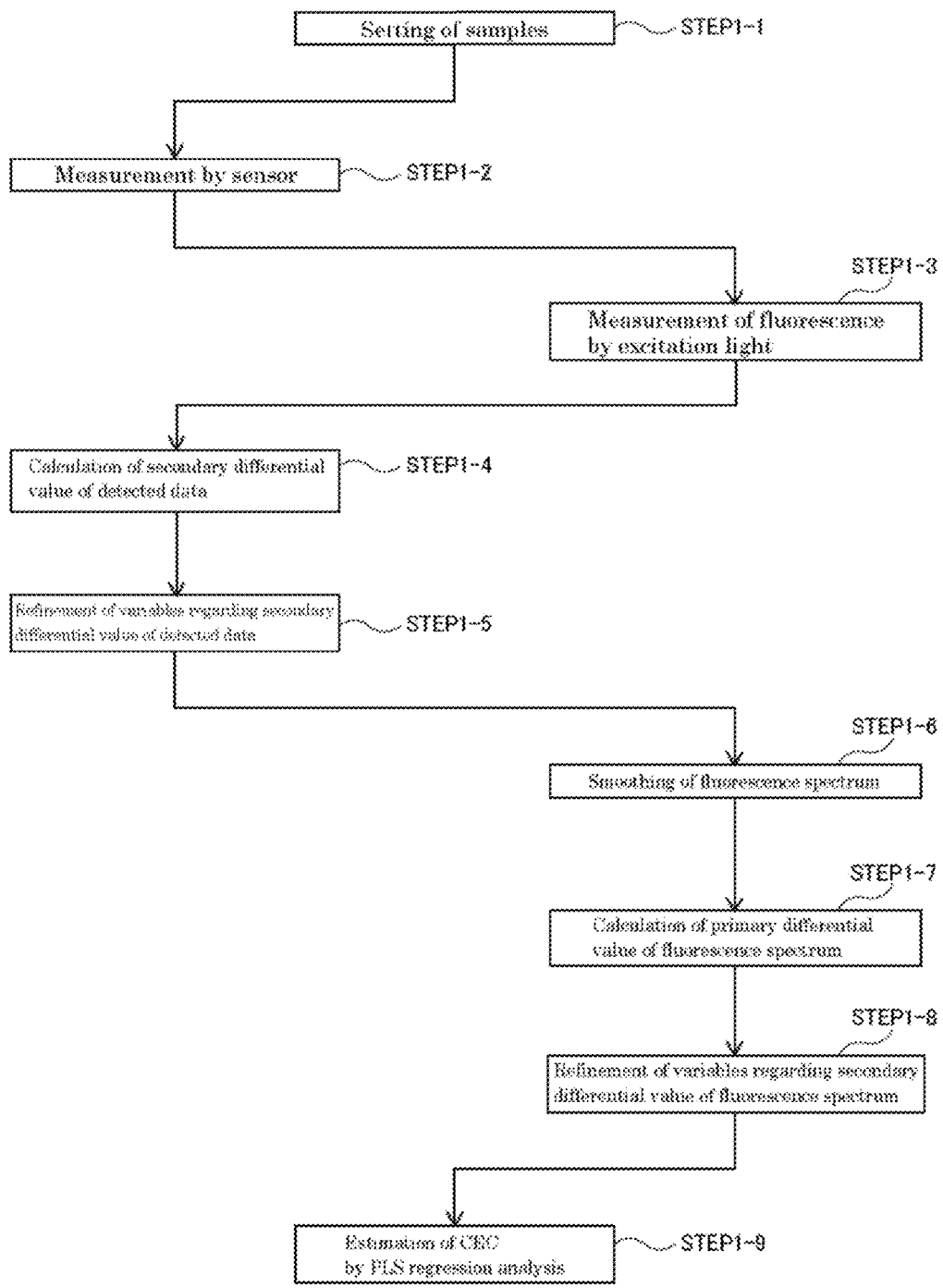

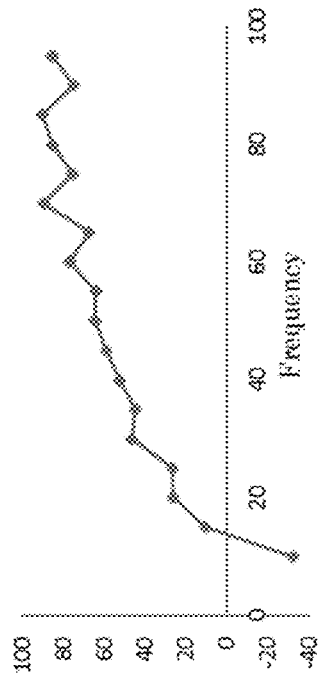
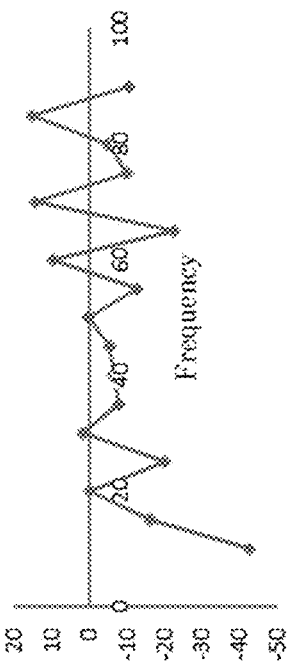
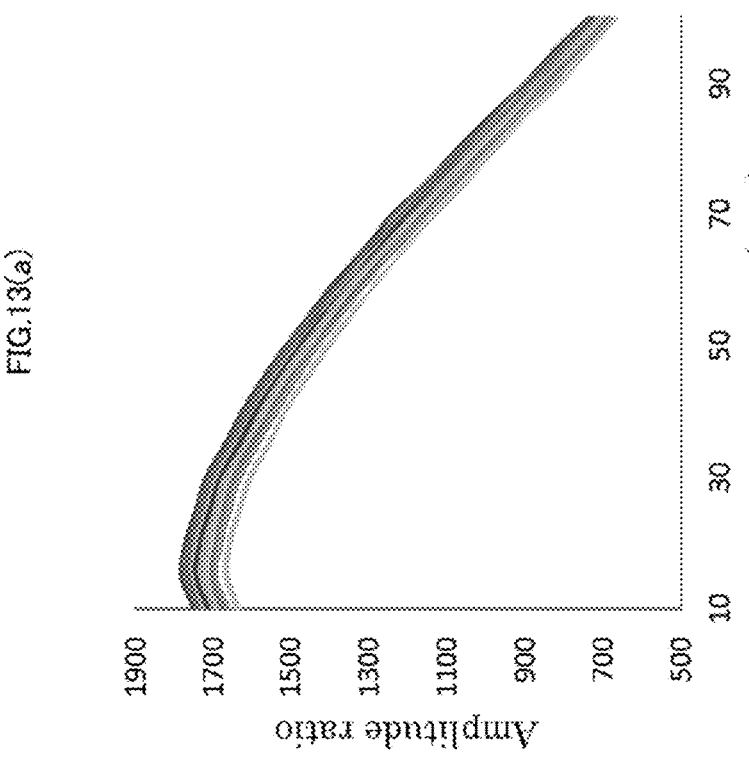

SOIL ANALYZING DEVICE AND SOIL ANALYZING METHOD

TECHNICAL FIELD

The present invention relates to a soil analyzing device and a soil analyzing method capable of finding indicators for assessing the fertility of the soil.

BACKGROUND ART

To increase the productivity of agricultural products, it is necessary to appropriately assess the fertility of the soil. Indexes that indicate the fertility of the soil include the soil fertility characteristics such as available nitrogen, available phosphoric acid, total phosphorus, total carbon, total nitrogen, K, Ca, Mg, Fe, Al, Na, CN ratio, and CEC (cation exchange capacity). To analyze the amount of available nitrogen, for example, methods of subjecting an organic liquid extracted from soil using a phosphate buffer solution to a visible absorption spectrophotometry or an ultraviolet absorption spectrophotometry, and using a near infrared reflectance spectrophotometry have been proposed. As a method of determining these indexes easily, some of the present inventors have proposed a method of illuminating the excitation light to the soil and analyzing the fluorescence spectrum from the soil, thereby estimating the fertility characteristics of the soil (Patent Literature 1).

CITATION LIST

Patent Literature

Patent Literature 1: JP 5885168 B

Non-Patent Literature

Non-patent Literature 1: "Standard Soil Analysis/Measurement Method" edited by the Standard Soil Analysis/Measurement Committee, Hakuyusha Co., Ltd., Nov. 15, 1986, pp. 150-154

SUMMARY OF INVENTION

Technical Problem

However, there is a problem that the cation exchange capacity (CEC), which is estimated by analyzing the fluorescence spectrum, cannot be determined as accurately as other soil fertility characteristics such as available nitrogen, available phosphoric acid, total carbon, total nitrogen, and CN ratio. In addition, since the fluorescence from the soil is measured, turbidity, etc., if any, in dispersing medium such as water that is used to measure the fluorescence in soil, there is a problem that the fluorescence cannot be measured smoothly.

In view of the above problems, the objective of the present invention is to provide a soil analyzing device and a soil analyzing method capable of determining the soil fertility characteristics including CEC accurately as indexes for assessing the fertility of the soil.

Solution to Problem

To achieve the above objective, the present invention has the following concept:

[1] A soil analyzing device including:
a sensor having a coil;
a measurement unit that generates an excitation signal to be input to the coil per frequency in order to apply an alternating magnetic field to the soil to be analyzed, and processes a detection signal output from the coil by applying the alternating magnetic field to the soil to be analyzed;
a storage unit that stores data concerning the correlation between a quantitative value of the soil fertility characteristics including CEC of two or more types of the soil having different components and an estimated value of soil fertility characteristics including CEC found from the processed detection signal measured by using the sensor and the measurement unit; and
an estimation unit that estimates the soil fertility characteristics including CEC of the soil to be analyzed based on the detection signal generated by allowing the sensor to apply the alternating magnetic field to the soil to be analyzed and processed using the measurement unit and by using the data stored in the storage unit.

[2] The soil analyzing device as set forth in [1], wherein the estimation unit estimates the soil fertility characteristics including CEC of the soil to be analyzed based on one or more items, of the processed detection signal itself output from the measurement unit, and the amplitude ratio and the phase difference between the excitation signal and the detection signal, that has (have) the correlation items with the soil fertility characteristics including CEC of the soil to be analyzed.

[3] The soil analyzing device as set forth in [1], wherein the estimation unit extracts items for estimating the soil fertility characteristics including CEC of the soil to be analyzed based on at least one of the following: one or more items, of the processed detection signal itself output from the measurement unit, and the amplitude ratio and the phase difference between the excitation signal and the detection signal; and either one, or both, of a primary differential value and a secondary differential value of the relevant item with respect to frequency.

[4] The soil analyzing device as set forth in [1], wherein the estimation unit finds a complex amplitude ratio with respect to the excitation signal based on the detection signal, and estimates the soil fertility characteristics by using a regression formula based on the regression analysis between the quantitative value of the soil fertility characteristics of different types of the soil stored in the storage unit and the complex amplitude ratio of the corresponding detection signal.

[5] The soil analyzing device as set forth in [4], wherein the complex amplitude ratio is represented by the absolute amplitude ratio and the phase difference, or by the real part and the imaginary part, and the regression formula has the absolute amplitude ratio and the phase difference, or the real part and the imaginary part, as independent variables respectively.

[6] The soil analyzing device as set forth in [1], wherein the estimation unit performs the partial least squares (PLS) regression analysis of two or more types of the soil having different components based on the quantitative value of the soil fertility characteristics including CEC and the detection signal obtained by allowing the sensor to apply the alternating magnetic field and processed using the measurement unit, and generates the data to be stored in the storage unit.

[7] A soil analyzing device, including:

a sensor having a coil;

a measurement unit that generates an excitation signal to be input to the coil in order to apply an alternating magnetic field to the soil to be analyzed and processes a detection signal output from the coil by applying the alternating magnetic field to the soil to be analyzed;

a light illumination unit that illuminates an excitation light to the soil to be analyzed;

a light measurement unit that measures a fluorescence from the soil to be analyzed, following the illumination of light from the light illumination unit;

a storage unit that stores data concerning correlation between a quantitative value of the soil fertility characteristics including CEC of two or more types of the soil having different components and an estimated value of the soil fertility characteristics including CEC found based on the processed detection signal measured using the sensor and the measurement unit, and the fluorescence spectrum data measured using the light illumination unit and the light measurement unit; and an estimation unit that estimates the soil fertility characteristics including CEC of the soil to be analyzed based on the detection signal generated by allowing the sensor to apply the alternating magnetic field and processed using the measurement unit, and the fluorescence spectrum data obtained by allowing the light illumination unit to illuminate the excitation light and measured by the measurement unit, and by using the data stored in the storage unit.

[8] The soil analyzing device as set forth in [7], wherein the estimation unit estimates the soil fertility characteristics of the soil to be analyzed based on one or more items, of the processed detection signal itself output from the measurement unit, and the amplitude ratio and the phase difference between the excitation signal and the detection signal, that has (have) the correlation items with the soil fertility characteristics including CEC of the soil to be analyzed, and based on the data having the correlation with the soil fertility characteristics including CEC of the soil to be analyzed, of the fluorescence spectrum data measured by the light measurement unit.

[9] The soil analyzing device as set forth in [7], wherein items for estimating the soil fertility characteristics including CEC of the soil to be analyzed are extracted based on at least one of the following: one or more items, of the processed detection signal itself output from the measurement unit, and the amplitude ratio and the phase difference between the excitation signal and the detection signal; and either one, or both, of the primary differential value and the secondary differential value of the relevant item with respect to frequency, and wherein the fluorescence spectrum data for estimating the soil fertility characteristics including CEC of the soil to be analyzed is extracted based on either one, or both, of the primary differential value and the secondary differential value, with respect to frequency, of the fluorescence spectrum data output from the light measurement unit.

[10] The soil analyzing device as set forth in [7], wherein the estimation unit performs the PLS regression analysis of two or more types of the soil having different components based on the quantitative value of the soil fertility characteristics including CEC, the detection signal obtained by allowing the sensor to apply the alternating magnetic field and processed using the measurement signal, and the fluorescence spectrum data obtained by allowing the light illumination unit to illuminate the excitation light and measured by the measurement unit, and generates the data to be stored in the storage unit.

[11] A soil analyzing method, including steps of:

generating an excitation signal by arbitrary frequencies and applying an alternating magnetic field to the soil to be analyzed;

finding a complex amplitude ratio to the excitation signal from a detection signal obtained from the magnetic field having permeated the soil; and estimating the soil fertility characteristics including CEC by a regression formula based on regression analysis between a quantitative value of the soil fertility characteristics including CEC of two or more different types of the soil and the complex amplitude ratio of a corresponding detection signal.

[12] The soil analyzing method as set forth in [11], wherein the complex amplitude ratio is represented by the absolute amplitude ratio and the phase difference, or the real part and the imaginary part, and the regression formula has the absolute amplitude ratio and the phase difference, or the real part and the imaginary part, as independent variables respectively.

[13] The soil analyzing method as set forth in [11] or [12], wherein the regression formula is generated by performing the PLS regression analysis based on the quantitative value of the soil fertility characteristics including CEC of two or more types of soil having different components and the detection signal obtained from the magnetic field having permeated the soil.

Advantageous Effects of Invention

According to the present invention, the soil analyzing device and the soil analyzing method capable of finding the soil fertility characteristics including CEC highly accurately as indicators for assessing the fertility of the soil can be provided.

BRIEF DESCRIPTION OF DRAWINGS

FIG. 2(a) is a chart showing the correlation of CEC with respect to the primary differential value of the detection signal itself with respect to frequency, FIG. 2(b) is a chart showing the correlation of CEC with respect to the primary differential value of the amplitude ratio, and FIG. 2(c) is a chart showing the correlation of CEC with respect to the primary differential value of phase difference.

FIG. 6 is an analysis flow chart according to Example 1.

FIG. 7(a) shows the frequency dependency of raw spectrum, FIG. 7(b) shows the frequency dependency of the primary differential value, FIG. 7(c) shows the frequency dependency of the secondary differential value, and FIG. 7(d)

shows the simple correlation between the secondary differential value and the quantitative CEC value.

Figure 8A:
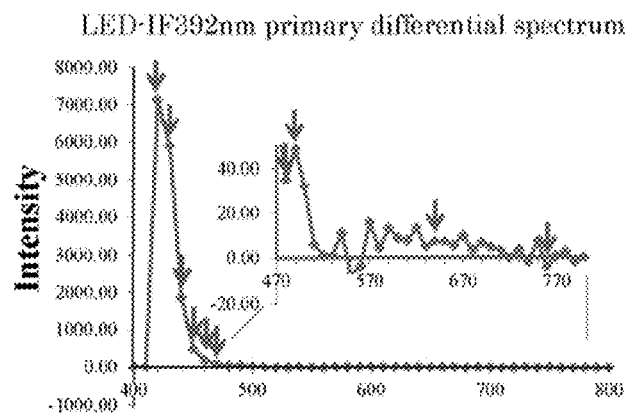
Figure 8B:
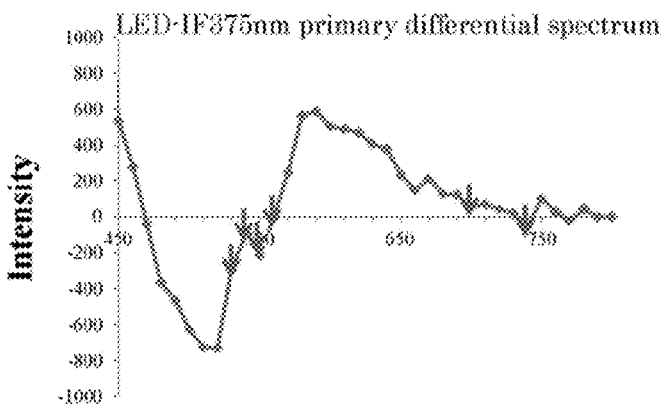
Figure 8C:
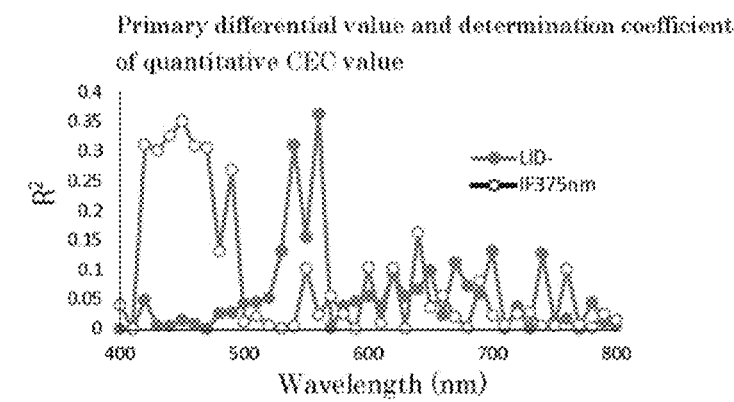

FIGS. 8(a), 8(b), and 8(c) are explanatory diagrams of Example 1 showing the refinement of explanatory variables concerning the fluorescence spectrum data, where FIG. 8(a) shows the frequency dependency of primary differential value of fluorescence spectrum due to 392 nm excitation light, FIG. 8(b) shows the frequency dependency of primary differential value of fluorescence spectrum due to 375 nm excitation light, and FIG. 8(c) shows the frequency dependency of the coefficient of determination $R^2$ of the primary differential value and the quantitative CEC value.

Figure 9:
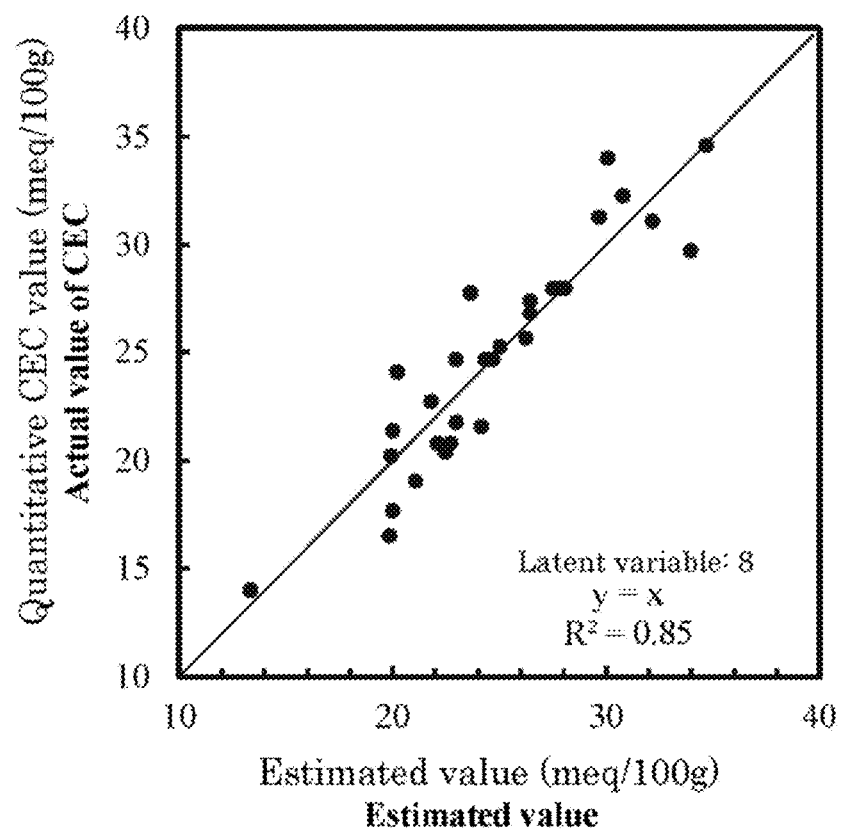

FIG. 9 shows the result of Example 1, detailing the relation between the estimated value and the quantitative value of CEC obtained when variables are refined.

Figure 10:
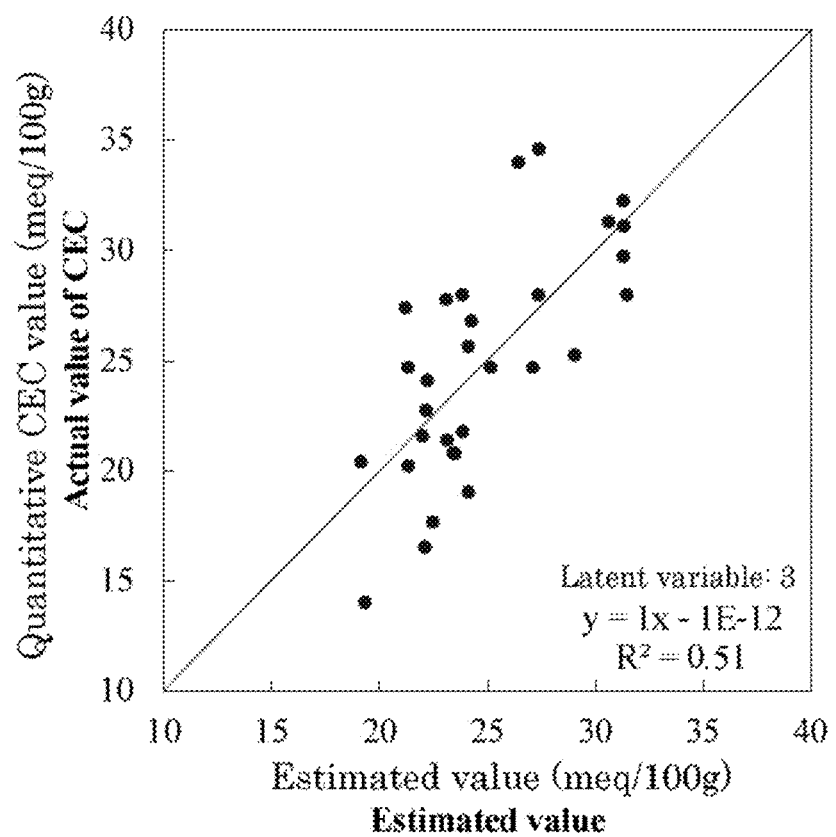

FIG. 10 is a chart showing the relation between the estimated value and the quantitative value of CEC obtained when variables are refined using the fluorescence data only as Comparative Example 1.

Figure 11:
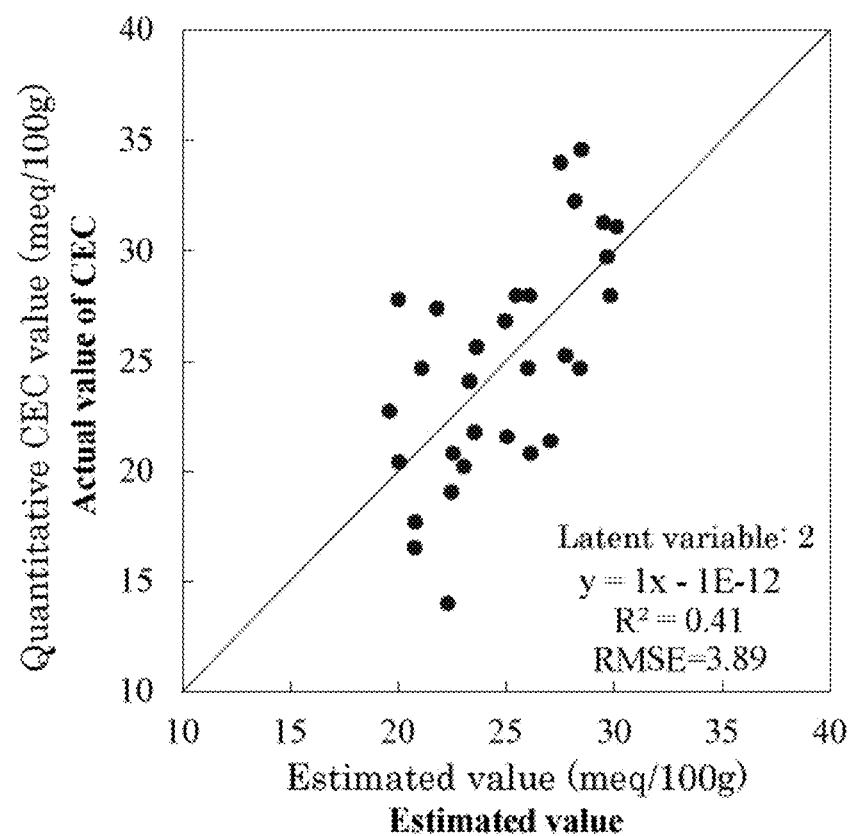

FIG. 11 is a chart showing the relation between estimated value and quantitative value of CEC obtained when variables are not refined using fluorescence only as Comparative Example 2.

Figure 12:
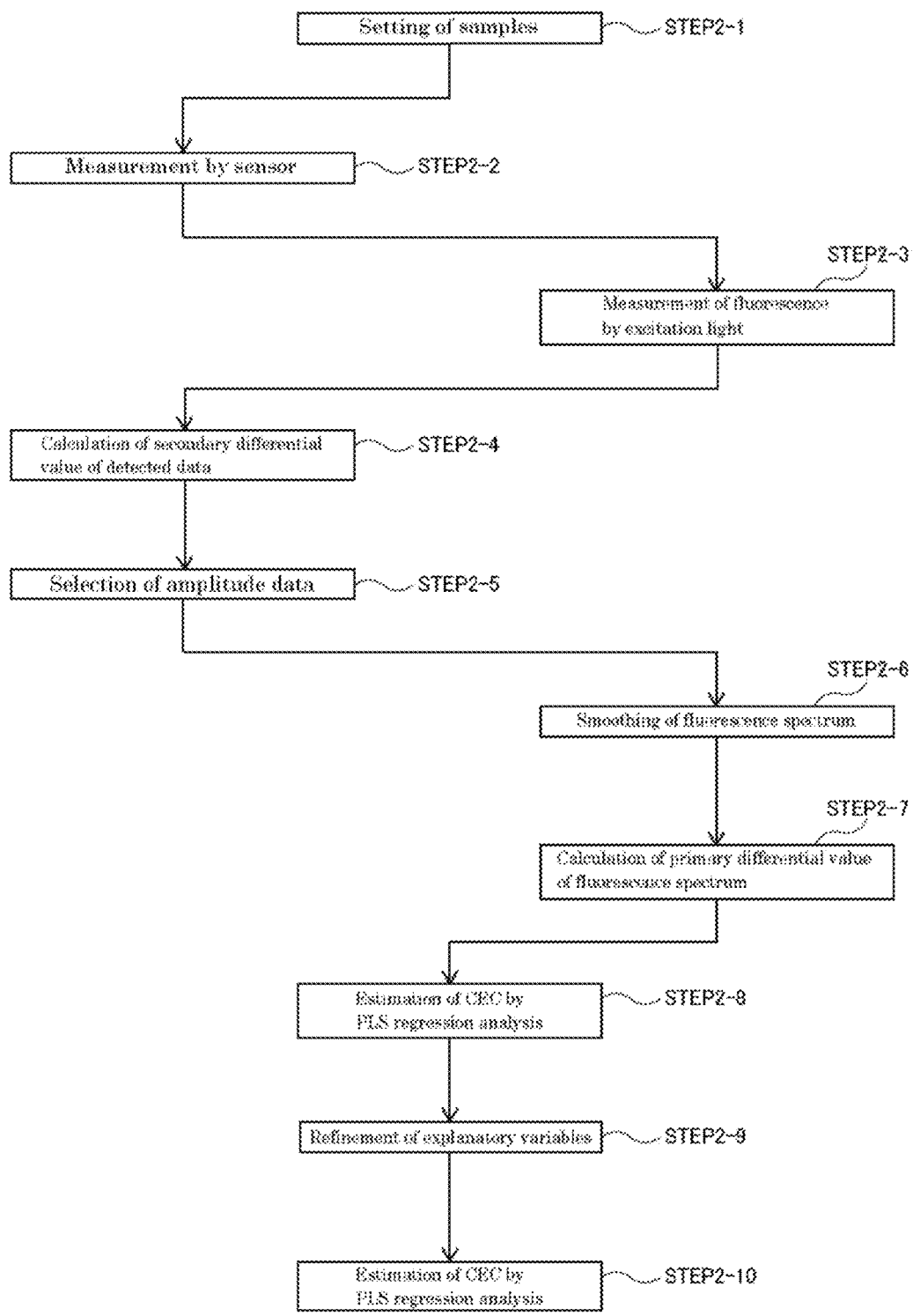

FIG. 12 is an analysis flow chart concerning Example 2.

FIGS. 13(a), 13(b), and 13(c) explain parts of the data processing process as shown in the flow chart in FIG. 12, where FIG. 13(a) shows the frequency dependency of amplitude ratio, FIG. 13(b) shows the frequency dependency of the primary differential value of the amplitude ratio, and FIG. 13(c) shows the frequency dependency of the secondary differential value of the amplitude ratio.

Figure 14:
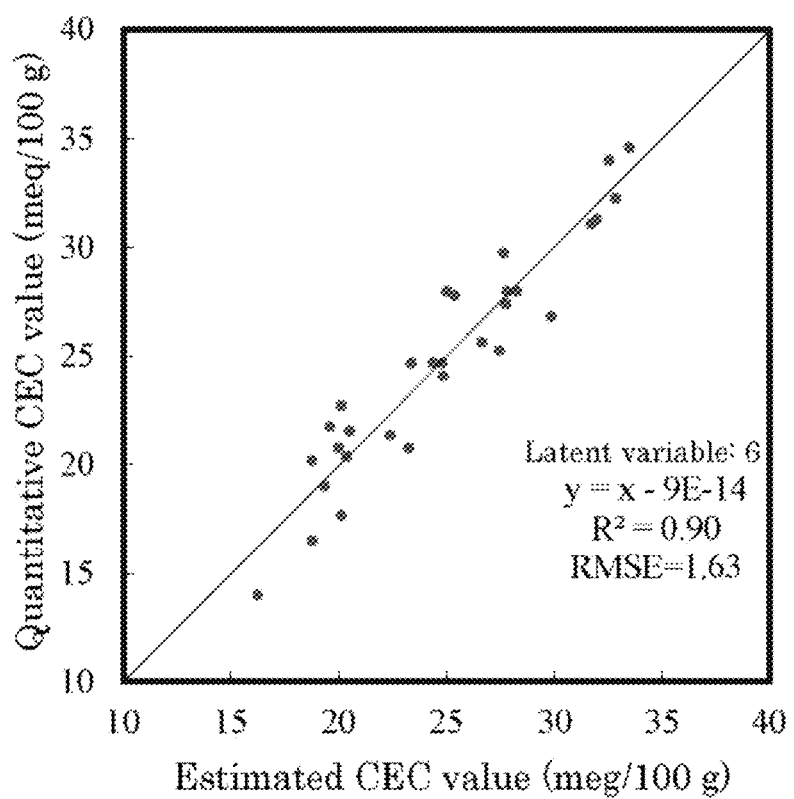

FIG. 14 is a chart showing the result of Example 2.

Figure 15:
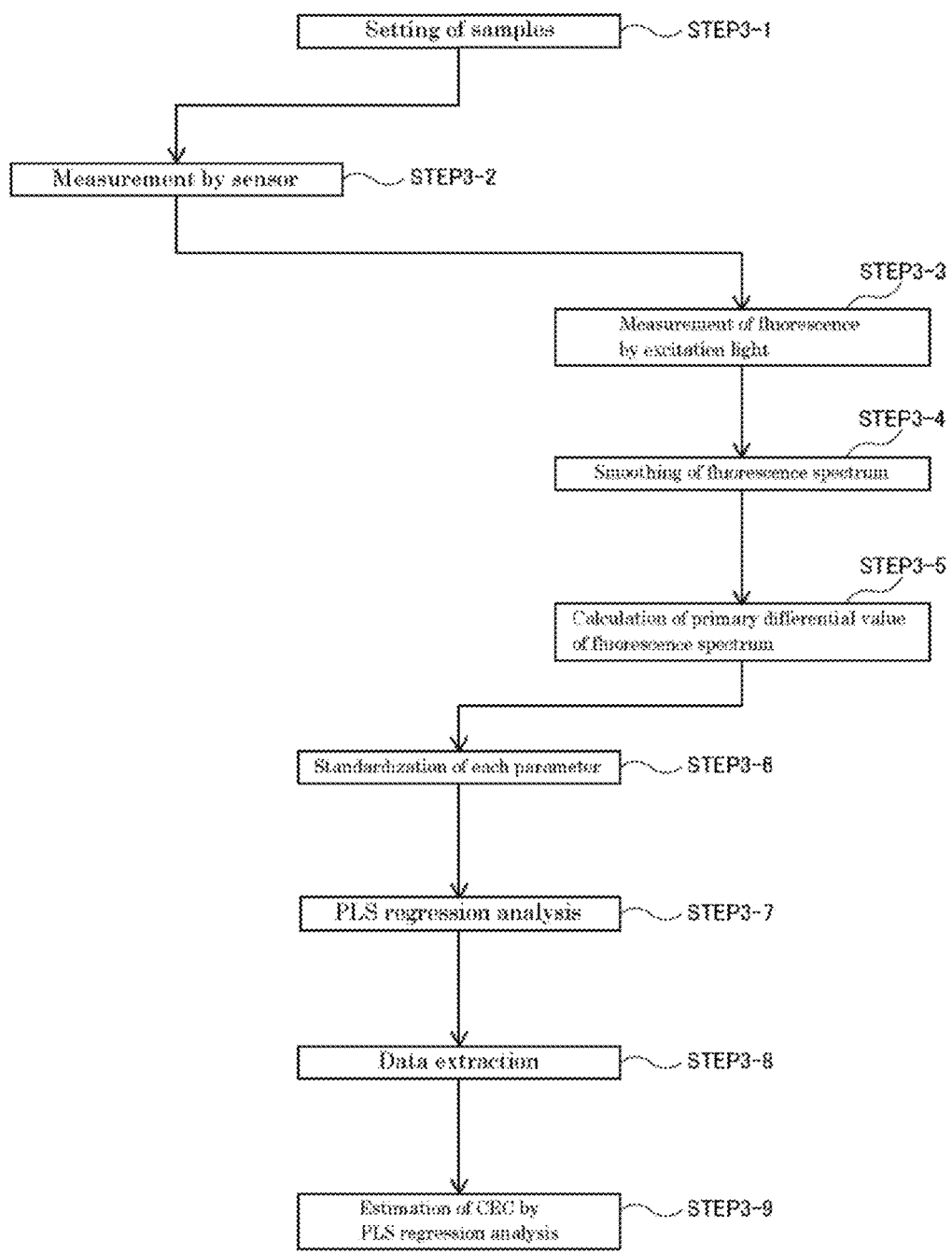

FIG. 15 is an analysis flow chart regarding Example 3.

Figure 16:
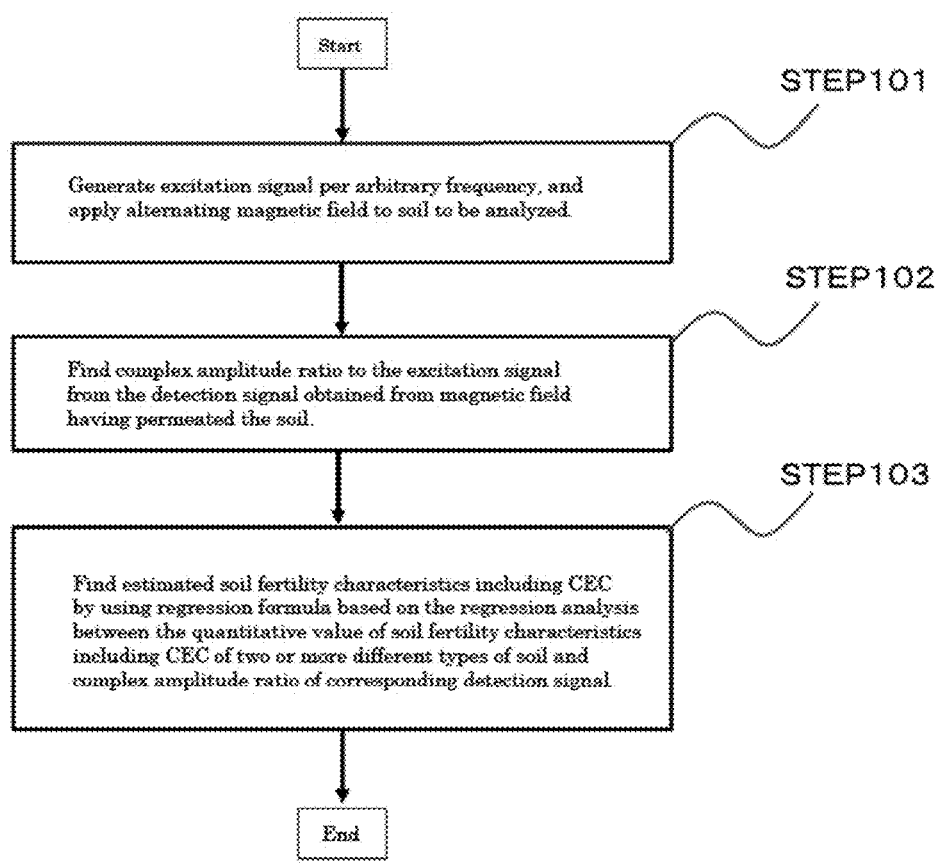

FIG. 16 is a chart showing the analysis flow regarding a third embodiment.

Figure 2A:
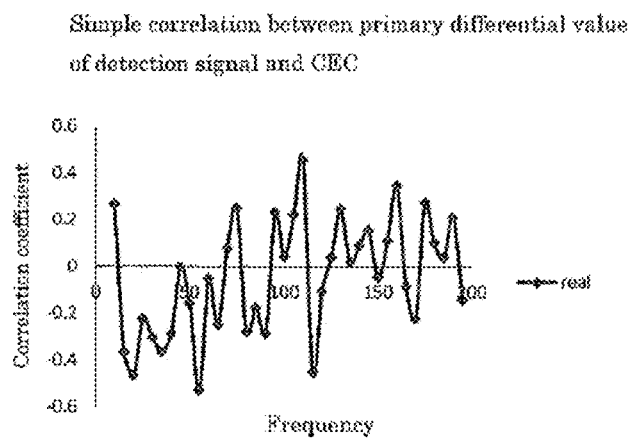
FIGS. 2(a), 2(b) and 2(c) show verification examples, where
Figure 2B:
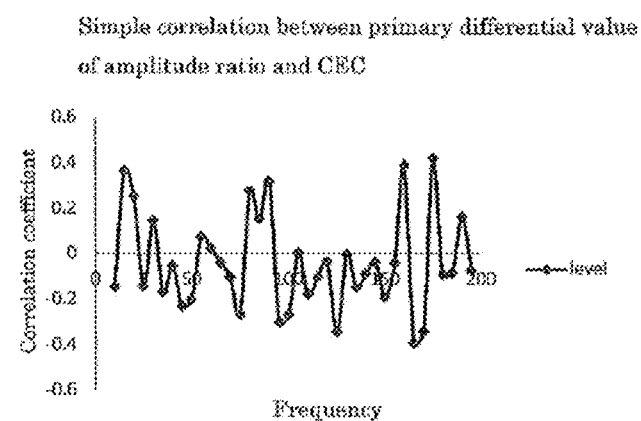
Figure 2C:
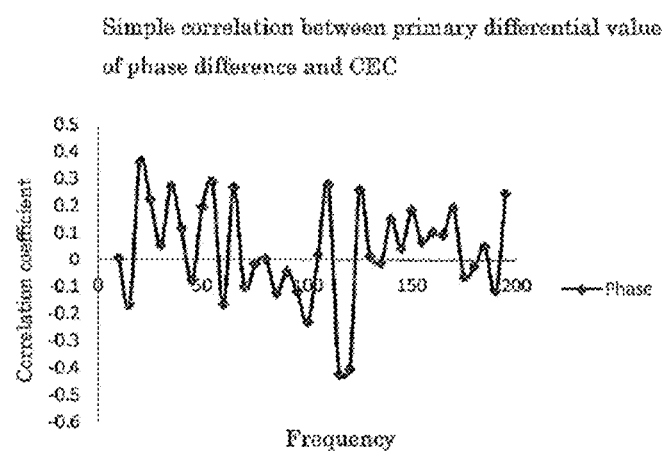
Figure 17:
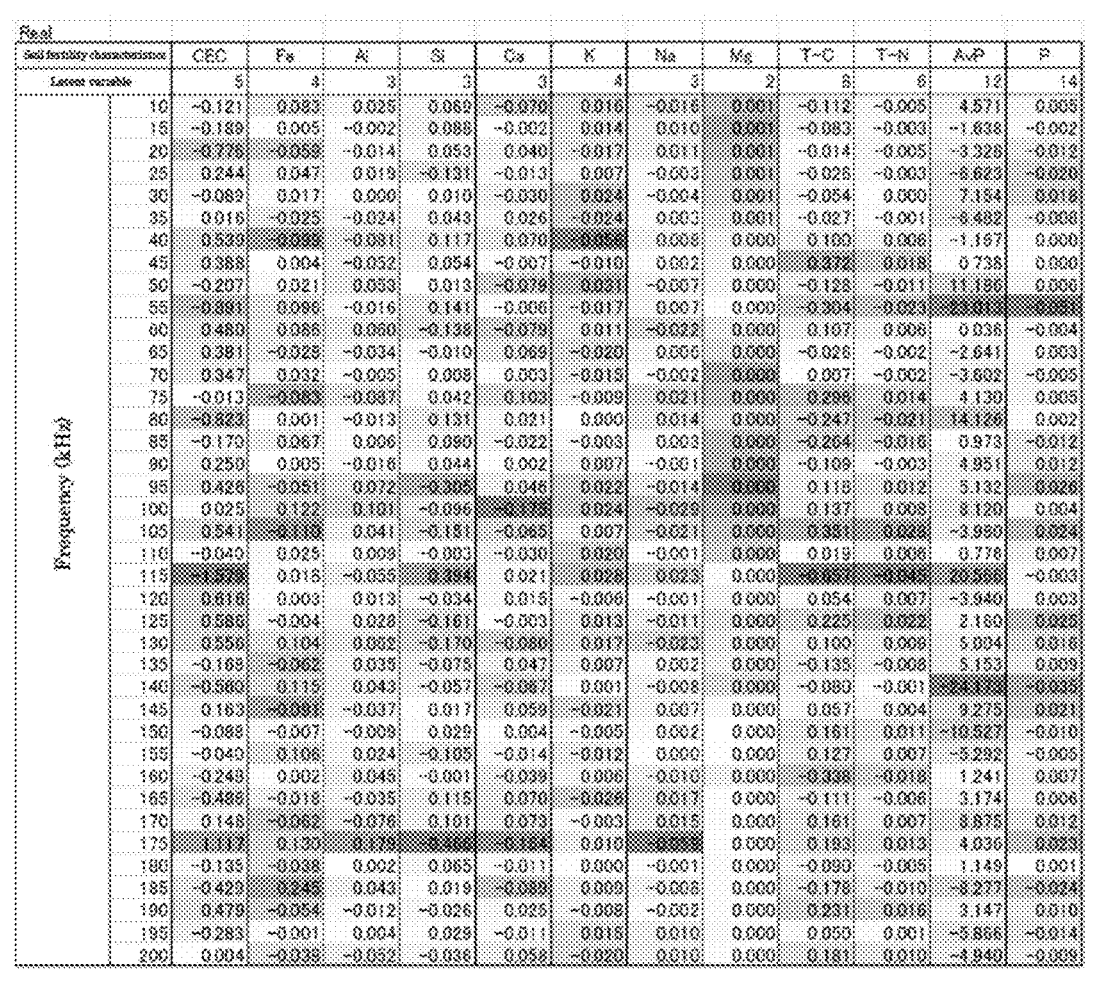

FIG. 17 is a chart showing the result of measurement of the PLS correlation coefficient of the real part performed directly without conducting the primary differentiation of the detection signal, unlike the first embodiment as shown in FIGS. 2(a), 2(b) and 2(c).

Figure 18:
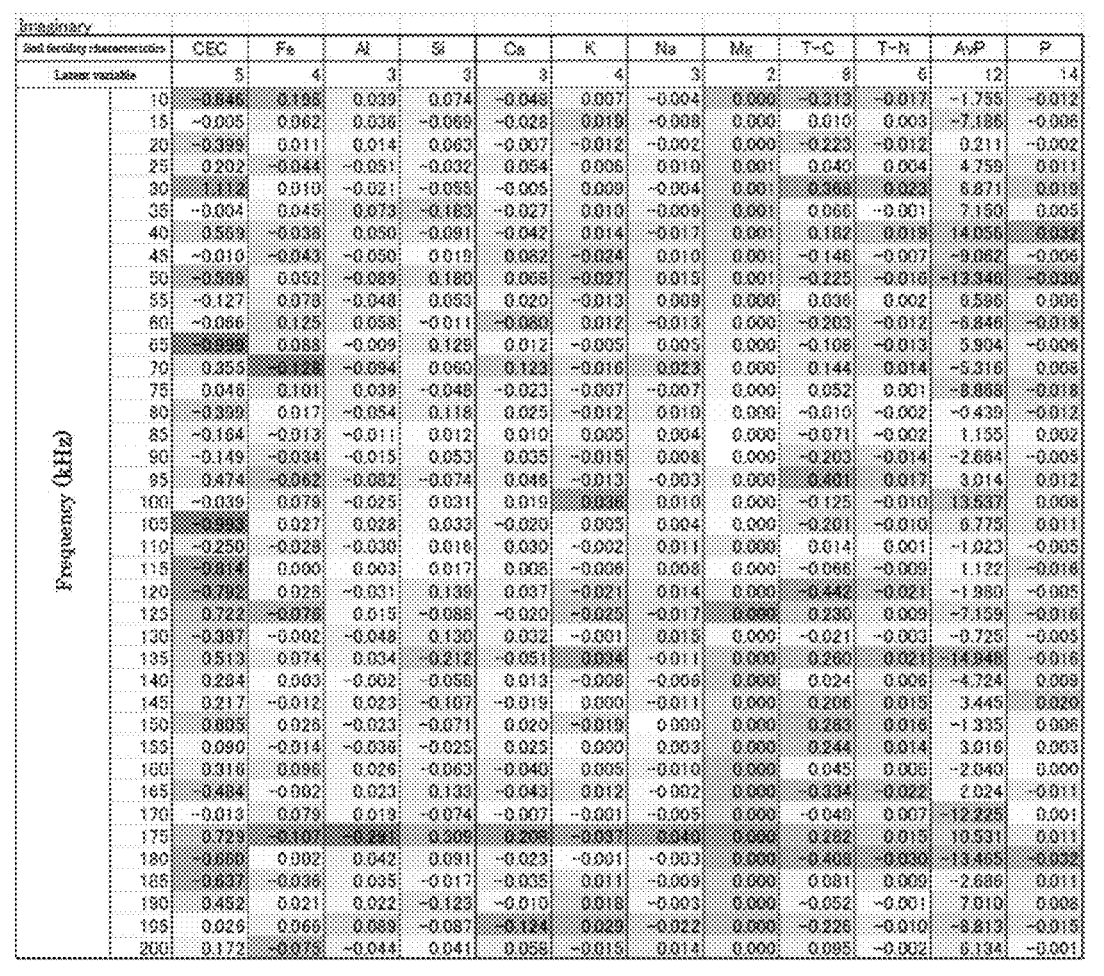

FIG. 18 is a chart showing the result of measurement of the PLS correlation coefficient of the imaginary part performed directly without conducting the primary differentiation of the detection signal, unlike the first embodiment as shown in FIGS. 2(a), 2(b) and 2(c).

Figure 19A:
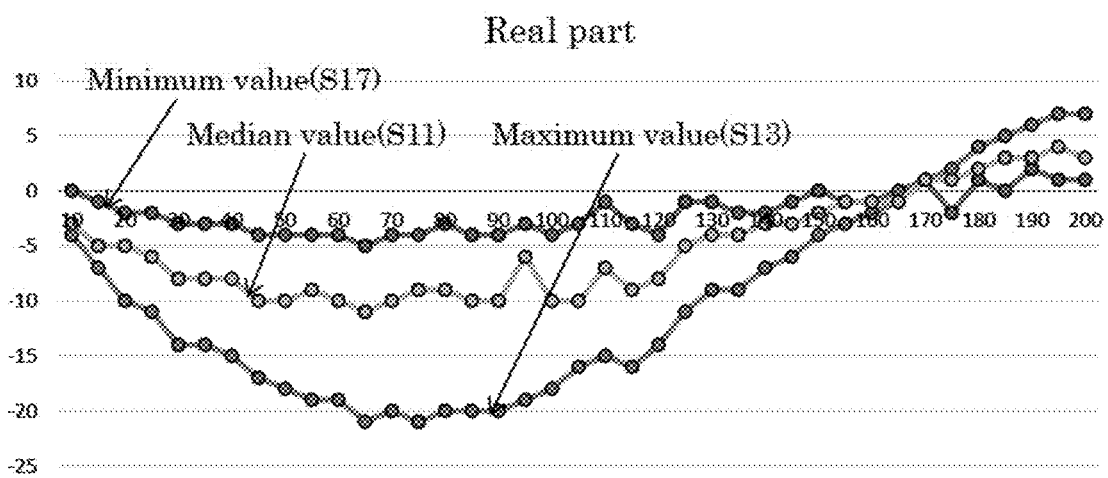
Figure 19B:
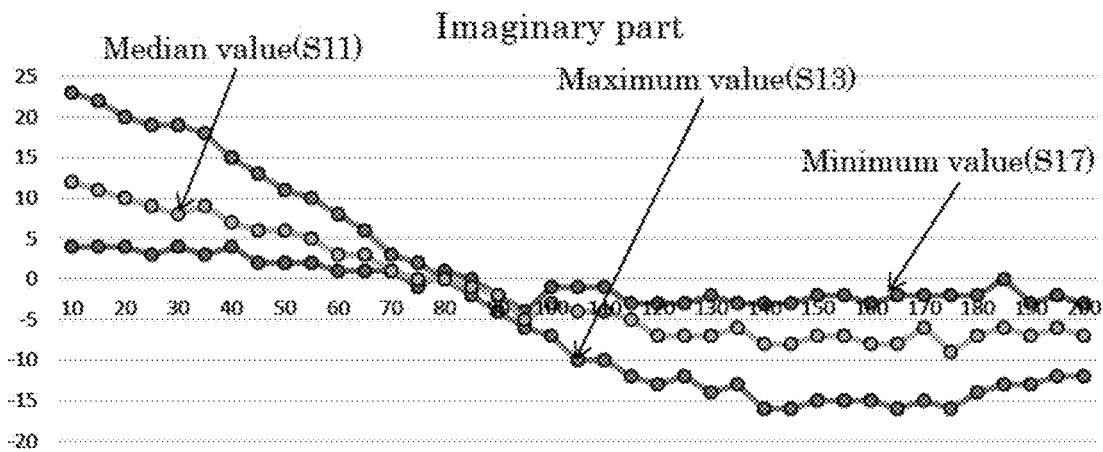

FIGS. 19(a), and 19(b), are examples of the frequency spectrum, with the amplitude obtained from the detection signal due to each permeating magnetic field of three samples having different iron contents displayed in intervals of 10 kHz within the range from 10 kHz to 200 kHz, wherein FIG. 19(a) represents the real part, and FIG. 19(b) represents the imaginary part.

Figure 20:
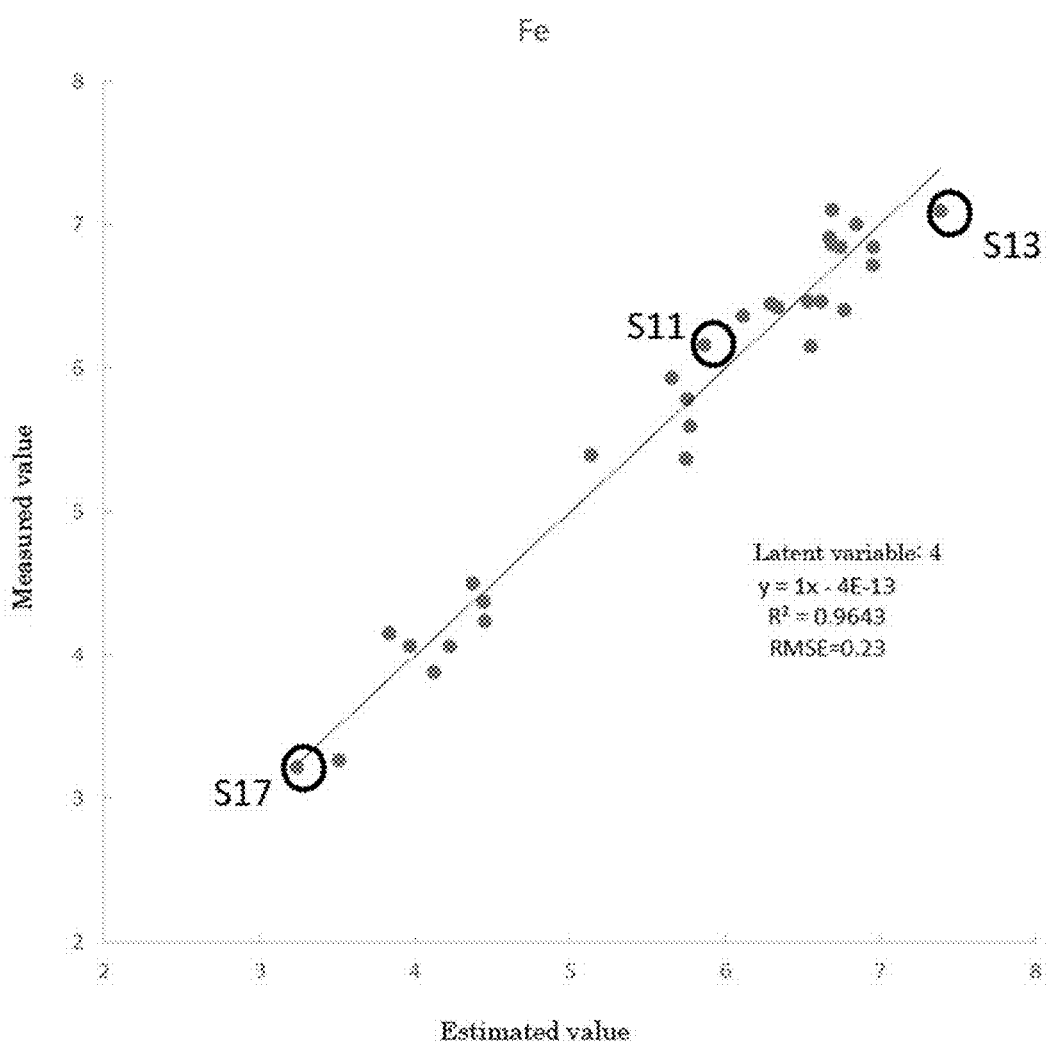

FIG. 20 is a chart showing the relation between the estimated value x and the quantitative value y of iron in Example 4.

Figure 21:
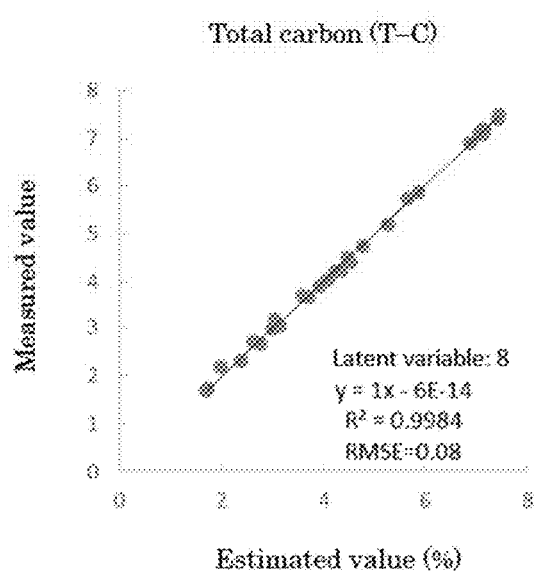

FIG. 21 is a chart showing the relation of the estimated value x and the quantitative value y of total carbon in Example 4.

Figure 22:
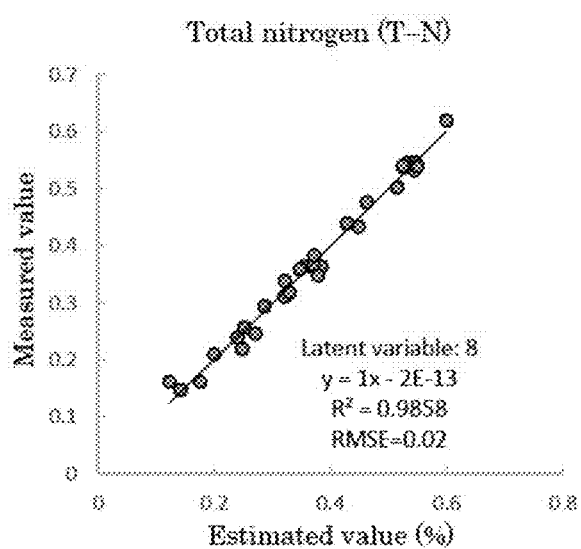

FIG. 22 is a chart showing the relation between the estimated value x and the quantitative value y of total nitrogen in Example 4.

Figure 23:
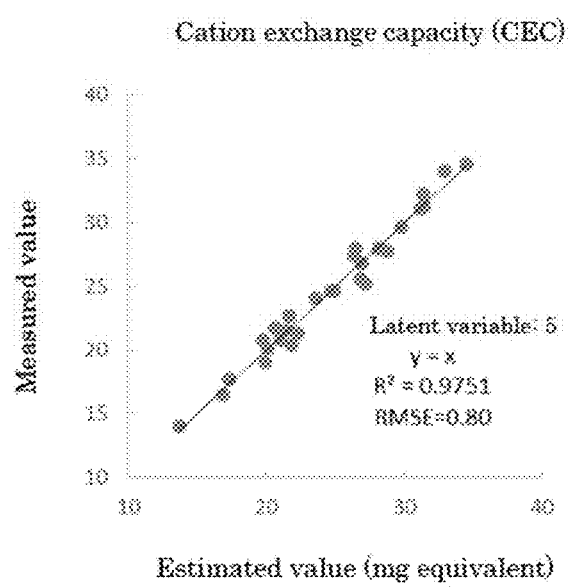

FIG. 23 is a chart showing the relation between the estimated value x and the quantitative value y of CEC in Example 4.

Figure 24:
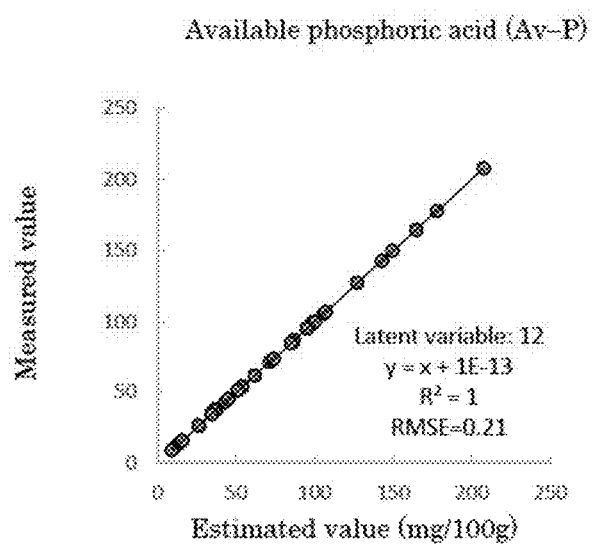

FIG. 24 is a chart showing the relation between the estimated value x and the quantitative value y of available phosphoric acid in Example 4.

Figure 25:
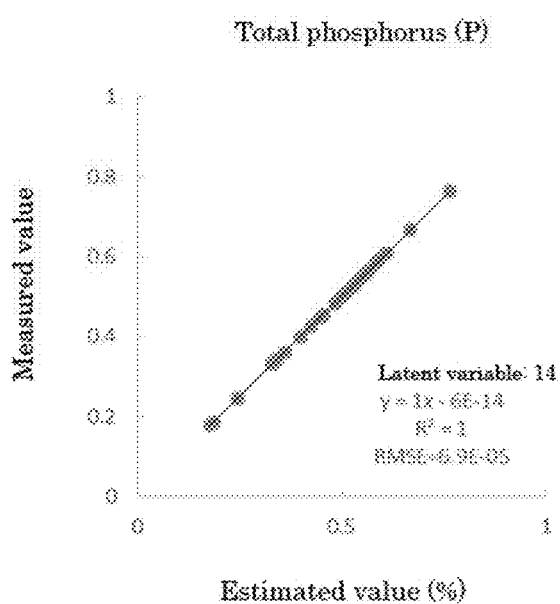

FIG. 25 is a chart showing the relation between the estimated value x and the quantitative value y of total phosphorus in Example 4.

Figure 26:
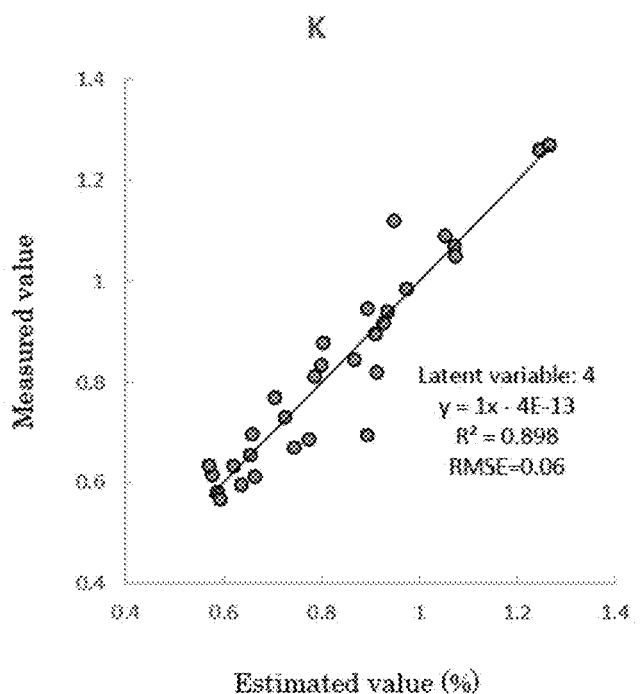

FIG. 26 is a chart showing the relation between the estimated value x and the quantitative vale y of potassium in Example 4.

Figure 27:
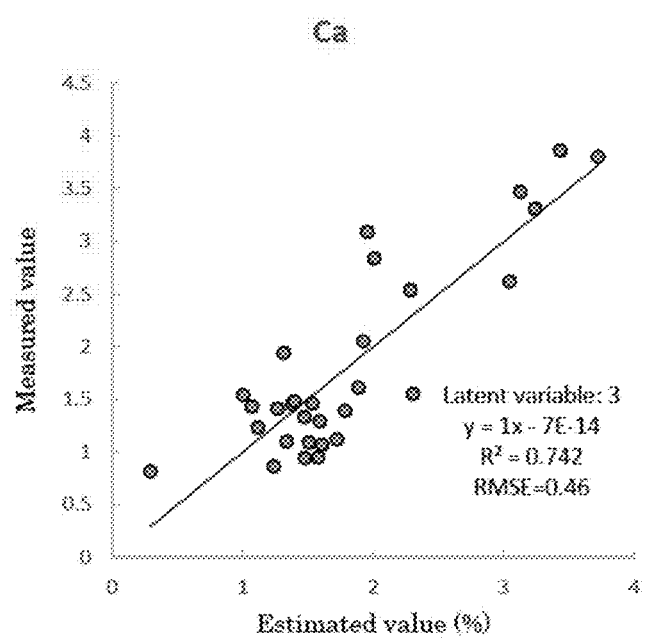

FIG. 27 is a chart showing the relation between the estimated value x and the quantitative value y of calcium in Example 4.

Figure 28:
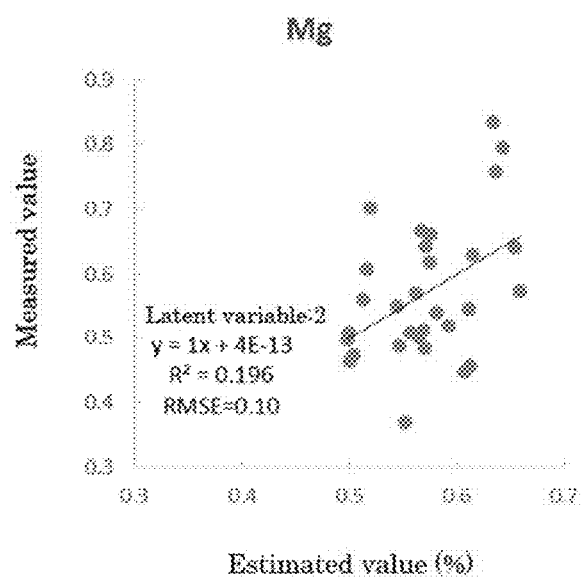

FIG. 28 is a chart showing the relation between the estimated value x and the quantitative value y of magnesium in Example 4.

Figure 29:
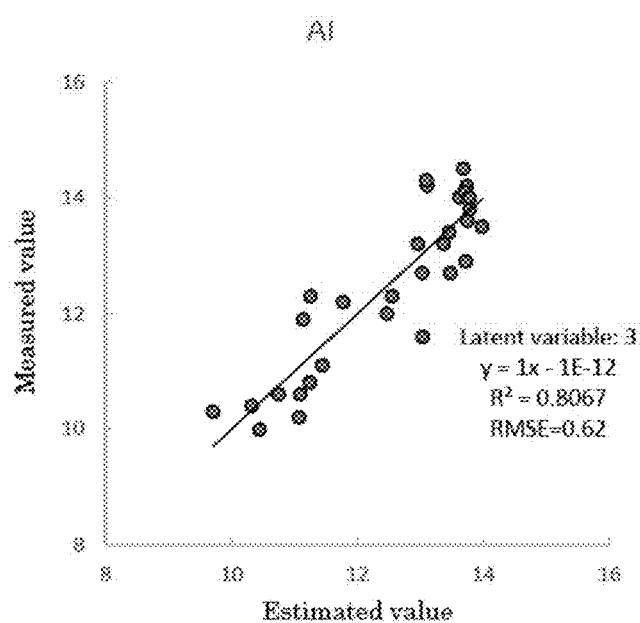

FIG. 29 is a chart showing the relation between the estimated value x and the quantitative value y of aluminum in Example 4.

Figure 30:
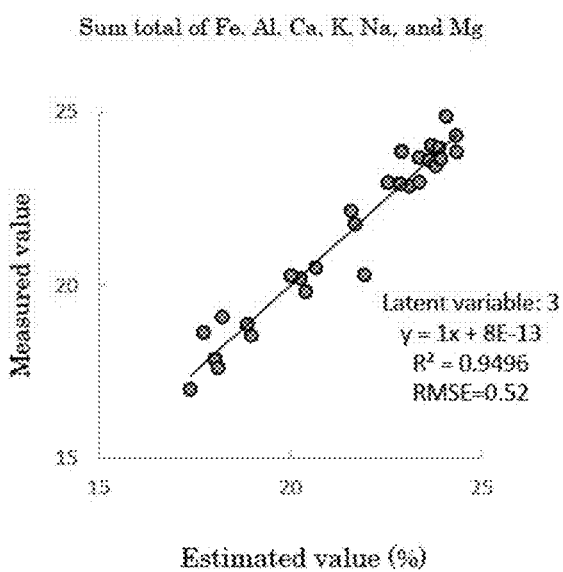

FIG. 30 is a chart showing the relation between the estimated value x and the quantitative value y of sum total of Fe, Al, Ca, K, Na, and Mg in Example 4.

DESCRIPTION OF EMBODIMENTS

Embodiments of the present invention will hereinafter be described by referring to drawings. The practice of the present invention, with changes made as required within the scope of the present invention, is allowed.

First Embodiment

Figure 1:
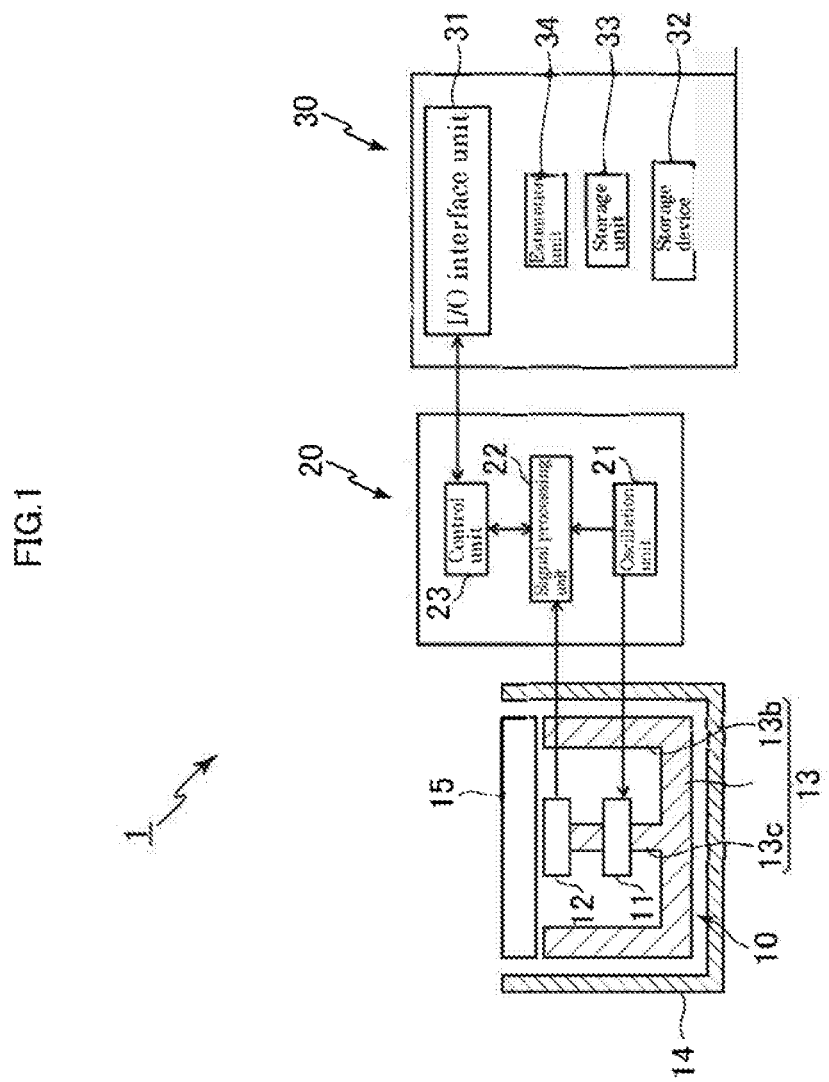
FIG. 1 is a block diagram of a soil analyzing device according to a first embodiment of the present invention.

FIG. 1 is a block diagram of a soil analyzing device according to a first embodiment of the present invention. The soil analyzing device 1 according to the first embodiment includes: a sensor 10; a measurement unit 20; and a data processing unit 30.

The sensor 10 includes: an excitation coil 11 and a detection coil 12 as coils; and a magnetic path forming part 13. The sensor 10 is housed in a metal sensor holder 14, for example, to be shut off from an external magnetic field, and at an opening of the sensor holder 14, a sample holder 15 is disposed. The sensor 10 is supported by a non-magnetic gap filler (not shown) within the sensor holder 14, for example. The magnetic path forming part 13 is made of a bottom portion 13a, a cylindrical portion 13b, and an axial portion 13c, for example, and the bottom portion 13a supports the cylindrical portion 13b and the axial portion 13c. The excitation coil 11 and the detection coil 12 are attached to the axial portion 13c. With the sensor 10, since the detection coil 12 and the sample holder 15 are disposed on the magnetic path formed by the excitation coil 11 and the magnetic path forming part 13, the signal detected by the detection coil 12 can be affected depending on the magnetic permeability, etc. of the target of analysis in the sample holder 15. The sensor 10 is only an example, and those having similar function are acceptable. For example, the excitation coil 11 and the detection coil 12 may be integrated as one coil.

The measurement unit 20 includes: an oscillation unit 21; a signal processing unit 22; and a control unit 23. The oscillation unit 21 repeatedly generates a signal of a certain frequency, and increases or decreases the frequency of the signal in stages. The signal generated from the oscillation unit 21 is branched into an excitation signal and a reference signal, the excitation signal is input to the excitation coil 11 and at the same time output to the signal processing unit 22 as the reference signal. The signal processing unit 22 calculates the temporal variation of the detection signal from the detection coil 12 with respect to the excitation signal by using the reference signal from the oscillation unit 21. The signal processing unit 22, which has a Fourier transformation function, transforms the signal on the time axis into a signal on the frequency axis. The signal processing unit 22 also digitizes the detection signal from the sensor 10, and outputs it to the data processing unit 30. The control unit 23 inputs/outputs data and various control signals to/from the data processing unit 30, and at the same time controls the oscillation unit 21 and the signal processing unit 22.

In this embodiment, the data processing unit 30 estimates the CEC of the soil, which is one of the soil fertility characteristics, based on the digital data on the detection signal processed by the signal processing unit 22. The data processing unit 30 includes: an input/output interface unit 31 that interfaces with the control unit 23; a storage device 32 that has a main storage device and an auxiliary storage device; an arithmetic device that performs processing such as four arithmetic operations, etc.; and a computer equipped with a control device that controls the storage device and the arithmetic device. Since data processing programs stored in the auxiliary storage device are extended to and executed by the processing device, the data processing unit 30 is equipped with a storage unit 33 and an estimation unit 34 as shown in FIG. 1 from a functional perspective.

The storage unit 33 stores the data concerning correlation between the quantitative CEC value and the estimated CEC value found based on processed detection signal measured using the sensor 10 and the measurement unit 20 concerning two or more types of soil having different components.

The estimation unit 34 allows the sensor 10 to apply an alternating magnetic field to the soil to be analyzed, and estimates the CEC of the soil to be analyzed using the data stored in the storage unit 33 based on the detection signal processed using the measurement unit 20.

It is desirable that the estimation unit 34 estimate the CEC of the soil to be analyzed based on an item or items, of the processed detection signal itself output from the measurement unit 20, and the amplitude ratio and the phase difference between the excitation signal and the detection signal, that have the correlation with the CEC of the soil to be analyzed.

Furthermore, it is also desirable that the estimation unit 34 extracts items for estimating the CEC of the soil to be analyzed based on at least one of the following: one or more items, of the processed detection signal itself output from the measurement unit 20, and the amplitude ratio and the phase difference between the excitation signal and the detection signal; and either one, or both of the primary differential value and the secondary differential value of the relevant item with respect to the frequency. Specifically, as the criteria for the estimation unit 34 to extract items for estimating the CEC of the soil to be analyzed based on at least one of the following: one or more items, of the processed detection signal itself output from the measurement unit 20, and the amplitude ratio and the phase difference between the excitation signal and the detection signal may be used firstly; and secondly, either one, or both, of the primary differential value and the secondary differential value of the relevant item with respect to the frequency may be used.

The estimation unit 34 performs the PLS regression analysis, regarding two or more types of soil having different components, based on the quantitative CEC value and the detection signal obtained by allowing the sensor 10 to apply the alternating magnetic field and measured by the measurement unit 20, and generates the data to be stored in the storage unit 33. Consequently, the estimation unit 34 may also be called the regression analysis unit.

A method of analyzing soil using the soil analyzing device 1 according to the embodiment of the present invention will be described below. Firstly, one type of the soil, or two or more types of the soil having different components, is/are prepared, air-dried, and crushed in a mortar. The air-dried and crushed soil was used as soil samples. With each of the soil samples, quantitative CEC value was found by the Schollenberger method, for example. Since the Schollenberger method is disclosed in Non-patent Literature 1, details are omitted here.

Each soil sample is put into the sensor holder 15 as shown in FIG. 1, and under the control of the control unit 23, the oscillation unit 21 is made to oscillate a signal at each frequency within a specified frequency range (from several kHz to several hundred kHz, for example) while increasing the frequency in stages in arbitrary frequency intervals (several kHz, for example), and output it to the excitation coil 11. The signal detected by the detection coil 12 is processed by the signal processing unit 22 by the signal at each frequency, transformed into a digital signal, and output to the data processing unit 30. The estimation unit 34 finds the correlation between the processed detection signal and the quantitative CEC value, and performs the PLS regression analysis. The obtained result is stored in the storage unit 33. When finding the correlation, items for estimating CEC are extracted based on at least one of the following: one or more items, of the detection signal itself, and the amplitude ratio and the phase difference between the excitation signal and the detection signal; and either one, or both, of the primary differential value and the secondary differential value of the relevant item with respect to the frequency. The preparation for analysis has thus been completed.

Similarly, the soil to be analyzed is air-dried, crushed in a mortar, and put into the sample holder 15. Under the control of the control unit 23, the oscillation unit 21 is made to oscillate the signal at each frequency within the specified frequency range (from several kHz to several hundred kHz, for example) while increasing the frequency in stages in arbitrary frequency intervals (several kHz, for example), and output it to the excitation coil 11. The signal detected by the detection coil 12 is processed by the signal processing unit 22 by the signal at each frequency, transformed into the digital signal, and output to the data processing unit 30. The estimation unit 34 estimates the CEC of the soil to be analyzed based on the processed detection signal output from the signal processing unit 22 and the data stored in the storage unit 33.

The estimation unit 34 finds estimated CEC value of the soil to be analyzed based on one or more items, of processed detection signal itself output from the measurement unit 20, and the amplitude ratio and the phase difference between the excitation signal and the detection signal, that has (have) the correlation with the CEC. The storage unit 33 stores quantitative CEC values of the two or more different types of soil, the detection signal itself of those types of soil processed by the signal processing unit 22, and regression formulae, average value, etc. concerning each item of the amplitude ratio and the phase difference. In other words, since the detection signal itself processed by the signal processing unit 22 as well as the amplitude ratio and the phase difference between the excitation signal and the detection signal of the soil to be analyzed are input from the signal processing unit 22, the CEC value can be estimated by finding how much each item is deviated from the statistical CEC value (the average value, for example) and adding the deviations from the statistical CEC value.

The CEC can also be estimated as follows. With the measurement unit 20, suppose that the excitation signal from the oscillation unit 21 is represented as $e_{in}=E_{in}e^{j(2\pi ft)}$, and that the detection signal input from the sensor 10 to the signal processing unit 22 is represented as $e_{out}=E_{out}e^{j(2\pi ft+\phi)}$ where $E_{in}$ and $E_{out}$ are the amplitude of the excitation signal and that of the detection signal, f is frequency, t is time, $\phi$ is phase difference, e is natural logarithm, and j is imaginary unit.

Then, the amplitude ratio of the detection signal to the excitation signal is represented as $E_{out}/E_{in}$, and the phase difference between the excitation signal and the detection signal is represented as $\phi$. Since the data processing unit 30 obtains the amplitude ratio and the phase difference from the detection signal itself, the real part or the imaginary part of $E_{out}e^{j(2\pi ft+\phi)}$, or the detection signal/excitation signal, one or more items, of the detection signal itself, and the amplitude ratio and the phase difference, is/are differentiated by frequency by n (≥1) times, and from those values, one having higher CEC correlation coefficient is selected. Consequently, the estimated CEC value is determined by the following formula.

The estimated CEC value=$f(\text{Real}(e_{in}), \text{IMa}(e_{in}), E_{out}/E_{in}, \phi, d^n e_{out}/df_n, d^n(E_{out}/E_{in})/df_n, d^n\phi/df_n)$ The estimated value is thus represented as a function of a parameter having the correlation, of the following seven parameters: $\text{Real}(e_{in})$, $\text{Ima}(e_{in})$, $E_{out}/E_{in}$, $\phi$, $d^n e_{out}/df_n$, $d^n(E_{out}/E_{in})/df_n$, $d^n\phi/df_n$.

(Verification of the Estimation of CEC of the Soil Using a Sensor)

It is then verified that the CEC value of the soil can be estimated accurately by using the soil analyzing device 1 according to the embodiment of the present invention, and by measuring the magnetic permeability of the soil as the detection signal using the sensor 10.

Using a PET container as the sample holder 15, 10 g of air-dried powder soil was set to the sensor 10 as shown in FIG. 1. The oscillation unit 21 of the measurement unit 20 was made to generate oscillation signals in 5-kHz intervals within a range from 10 kHz to 200 kHz, the signals are output to the excitation coil 11, and the detection signals from the detection coil 12 were obtained by the signal processing unit 22. The signal processing unit 22 was able to obtain 3 pieces of data per frequency, and data for 39 frequencies regarding the detection signal itself, the amplitude ratio, and the phase difference. Specifically, 39 pieces of data were obtained for each of the parameter per sample, and 117 pieces of data per sample were obtained.

Next, differential values of those data were then calculated in 5-kHz intervals within the range from 10 kHz to 100 kHz. In other words, 19 pieces of data were obtained for each of the parameter per sample, and 57 pieces of data per sample were obtained.

Next, the PLS regression analysis was performed with the calculated primary differential value used as an explanatory variable, and the quantitative CEC value measured by the Schollenberger method used as the objective variable. When each of n(≥1) pieces of detection signals themselves, the phase difference, the amplitude ratio values, and values based on this value (differential value, for example) are used as the explanatory variables, and the desired variable is set as the objective variable, the objective variable is found that minimized the sum of n pieces of square of difference between the objective variable and each explanatory variable. Other (n−1) pieces of estimated CEC values of the soil can be found by normalizing the found objective variable using one specific value of the soil (CEC value) obtained by the Schollenberger method.

Figure 3:
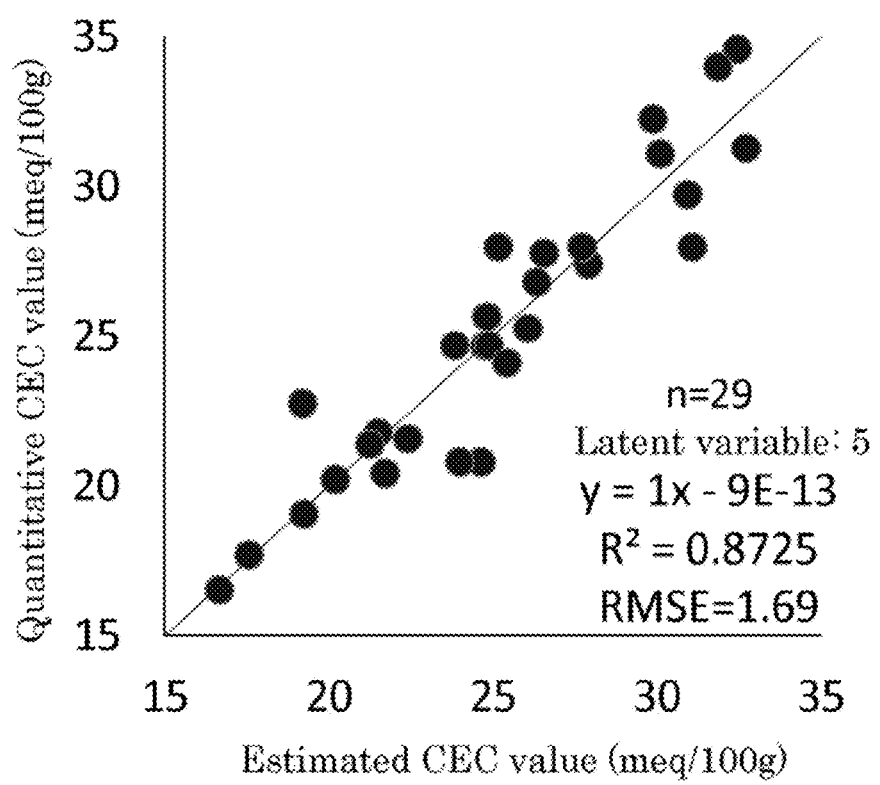
FIG. 3 shows the verification example, indicating the relation between an estimated CEC value and a quantitative value.

FIG. 2(a) is a chart showing the correlation of CEC with respect to the primary differential value of the detection signal itself with respect to frequency, FIG. 2(b) is a chart showing the correlation of CEC with respect to the primary differential value of the amplitude ratio, and FIG. 2(c) is a chart showing the correlation of CEC with respect to the primary differential value of the phase difference. These values were calculated and the estimated CEC values were calculated. FIG. 3 is a chart showing the relation between the estimated CEC value x and the quantitative CEC value y. The number of samples n were 29, latent variables were 5, the correlation was expressed as $y=x-9\times10^{-13}$, the coefficient of determination $R^2$ was 0.8725, and the root mean squared error (RMSE) was 1.69.

Figure 4:
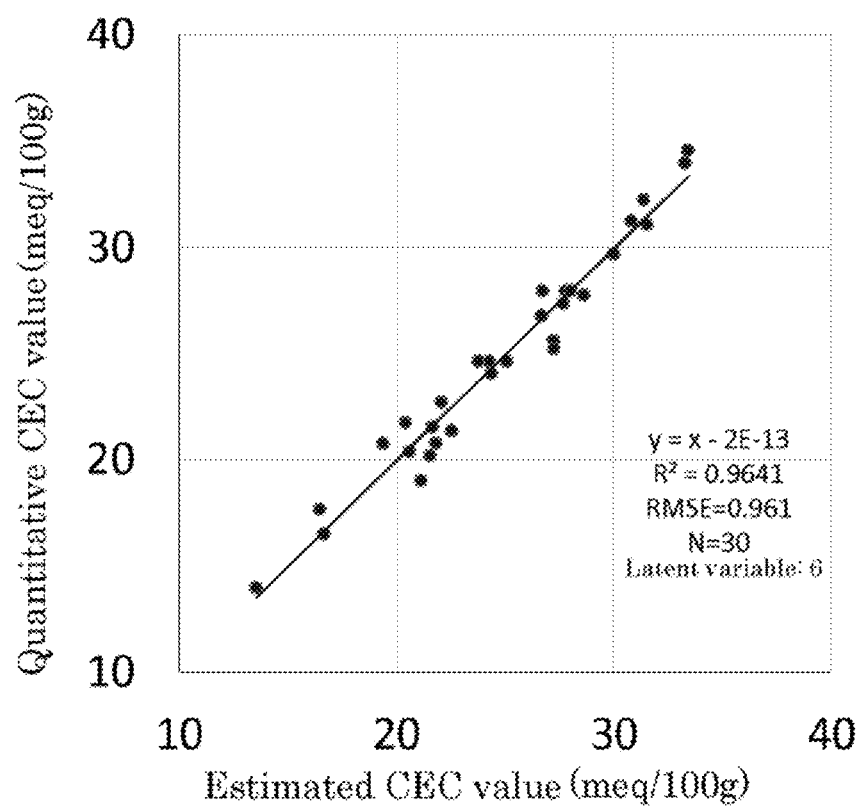
FIG. 4 shows the verification example, indicating the relation between the estimated CEC value and the quantitative value that is different from that shown in FIG. 3.

Furthermore, as a result of performing the PLC regression analysis in the same manner by changing the frequency from 10 kHz to 200 kHz, the chart in FIG. 4 showing the relation between the estimated CEC value x and the quantitative CEC value y was obtained, where the number of samples were 30, latent variables were 6, the correlation was expressed as $y=x-2\times10^{-13}$, the coefficient of determination $R^2$ was 0.9641, and the RMSE was 0.961. Therefore, the accuracy was improved by setting the frequency to a more preferable range.

Second Embodiment

Figure 5:
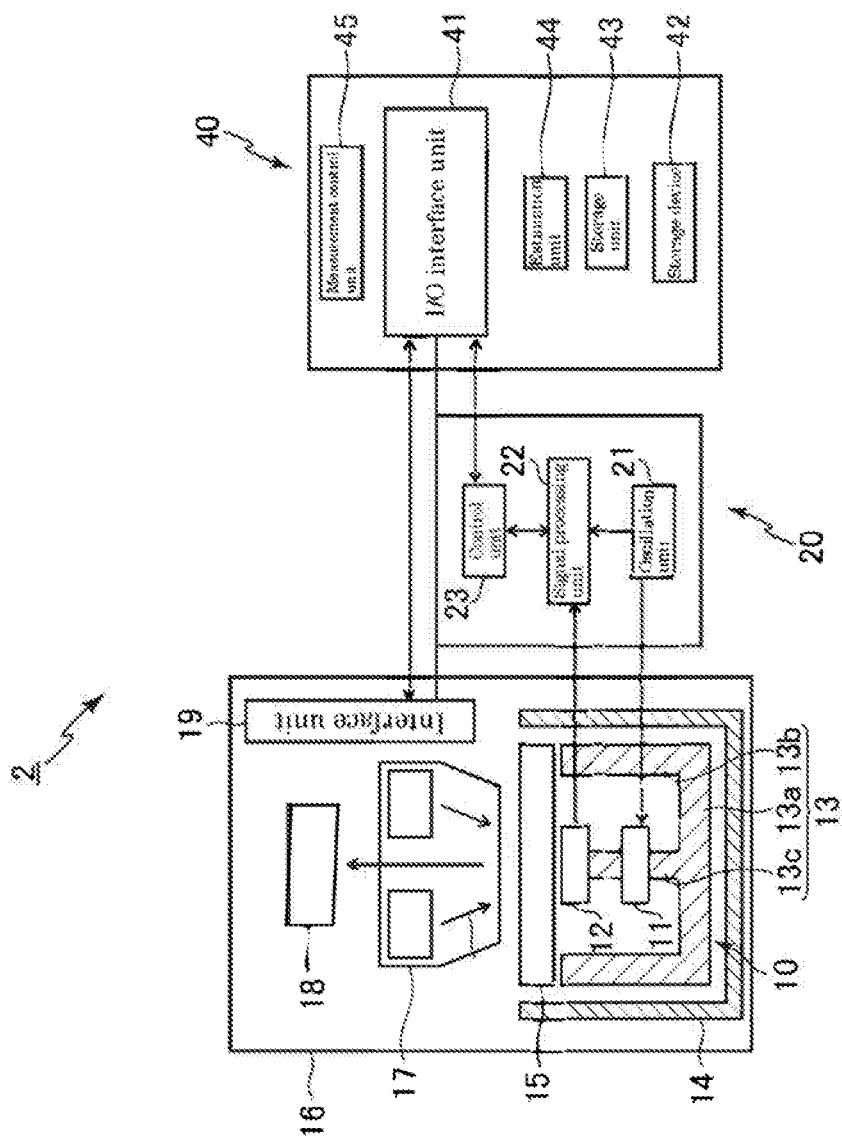
FIG. 5 is a block diagram of a soil analyzing device according to a second embodiment of the present invention.

FIG. 5 is a block diagram of a soil analyzing device according to a second embodiment of the present invention. The soil analyzing device 2 according to the second embodiment includes: the sensor 10; the measurement unit 20; and a data processing unit 40. The structure of the soil analyzing device 2 according to the second embodiment differs from the soil analyzing device 1 as shown in FIG. 1 in the following respect.

The sensor 10 is housed in a dark box 16, wherein a light illumination unit 17 and a light measurement unit 18 are disposed so as to face the sample holder 15, and an interface unit 19 is provided. It is only necessary that by illuminating excitation light to the soil placed in the sample holder 15, a fluorescence can be measured, the magnetic field can be applied by the excitation coil 11, and the detection can be performed by the detection coil 12. For example, as shown in FIG. 1, it is only necessary that the sensor 10 is placed on one side of the sample holder 15, and that the light illumination unit 17 and the light measurement unit 18 are placed on the other side. In particular, since the sample holder 15 is not covered even if the soil is placed in it, the light illumination unit 17 and the light measurement unit 18 are placed on the upper side, and the sensor 10 is placed on the lower side.

The light illumination unit 17, which is equipped with a light source that emits the excitation light, illuminates the excitation light to the sample placed in the sample holder 15. The light measurement unit 18, which is equipped with a spectrograph and a photodetector, for example, measures the fluorescence from the soil placed in the sample holder 15. The interface unit 19 controls the light illumination unit 17 and the light measurement unit 18, and at the same time outputs the fluorescence spectrum data measured by the light measurement unit 18 to the data processing unit 40.

The data processing unit 40 processes the detection signal data having been processed by the signal processing unit 22 of the measurement unit 20, and the fluorescence spectrum data having been processed by the light measurement unit 18. The data processing unit 40 includes: an input/output interface unit 41 that interfaces between the control unit 23 and the interface unit 19; a storage device 42 that has a main storage device and an auxiliary storage device; an arithmetic device that performs processing such as four arithmetic operations, etc.; and a computer equipped with a control device that controls the storage device and the processing device. Since data processing programs stored in the auxiliary storage device are extended to and executed by the arithmetic device, the data processing unit 40 is equipped with a storage unit 43 and an estimation unit 44 as shown in FIG. 5 from a functional perspective. It is also equipped with a measurement control unit 45, which controls the light illumination unit 17 and the light measurement unit 18.

The storage unit 43 stores the data concerning the correlation between the quantitative values of the soil fertility characteristics including CEC of two or more types of soil having different components, and the estimated values of the soil fertility characteristics including CEC found based on the processed detection signal measured by using the sensor 10 and the measurement unit 20, and the fluorescence spectrum data measured by using the light illumination unit 17 and the light measurement unit 18.

The estimation unit 44 estimates the soil fertility characteristics including CEC of the soil to be analyzed by using the data stored in the storage unit 43 based on the detection signal generated by allowing the sensor 10 to apply the alternating magnetic field to the soil to be analyzed and processed by the measurement unit 20 and the fluorescence spectrum data obtained by allowing the light illumination unit 17 to illuminate excitation light and measured by the light measurement unit 18.

The estimation unit 44 estimates the soil fertility characteristics of the soil to be analyzed based on one or more items, of the processed detection signal itself output from the measurement unit 20, and the amplitude ratio and the phase difference between the excitation signal and the detection signal, that has (have) correlation with the soil fertility characteristics including CEC of the soil to be analyzed, and based on the data having correlation with the soil fertility characteristics including CEC of the soil to be analyzed, of the fluorescence spectrum data measured by the light measurement unit 18.

It is desirable that the estimation unit 44 extract items for estimating the soil fertility characteristics including CEC of the soil to be analyzed based on at least one of the following: one or more items, of the processed detection signal itself output from the measurement unit 20, and the amplitude ratio and the phase difference between the excitation signal and the detection signal; and either one, or both, of the primary differential value and the secondary differential value of the relevant item with respect to frequency. It is also desirable that the estimation unit 44 extract the fluorescence spectrum data for estimating the soil fertility characteristics including CEC of the soil to be analyzed based on either one, or both, of the primary differential value and the secondary differential value of the fluorescence spectrum data with respect to frequency.

The estimation unit 44 performs the PLS regression analysis of two or more types of soil having different components based on the quantitative values of the soil fertility characteristics including the CEC, the detection signal generated by allowing the sensor 10 to apply the alternating magnetic field and processed by using the measurement unit 20, and the fluorescence spectrum data obtained by allowing the light illumination unit 17 to illuminate excitation light and measured by the light measurement unit 18, and the estimation unit 44 generates data to be stored in the storage unit 43. Consequently, the estimation unit 44 may also be called the regression analysis unit.

A method of analyzing soil using the soil analyzing device 2 according to the embodiment of the present invention will be described below. By this method, as the soil fertility characteristics, not only CEC but also any one, or two or more combinations, of available nitrogen, available phosphoric acid, total nitrogen, total carbon, and CN ratio, can be found. The method of estimating CEC of the soil to be analyzed will be described first.

As in the case of the soil analyzing method using the soil analyzing device 1 as shown in FIG. 1, one or more types of soil having different components is/are prepared, air-dried, and crushed in a mortar, and the air-dried crushed soil was used as soil samples. Then, the quantitative CEC value of each soil sample was found by the Schollenberger method, for example. Since the Schollenberger method is disclosed in Non-patent Literature 1, detailed description is omitted here.

Each soil sample is put into the sensor holder 15 as shown in FIG. 5, and under the control of the control unit 23, the oscillation unit 21 is made to oscillate a signal at each frequency within a specified frequency range (from several kHz to several hundred kHz, for example) while increasing the frequency in stages in arbitrary frequency intervals (several kHz, for example), and to output it to the excitation coil 11. The signal detected by the detection coil 12 is processed by the signal processing unit 22 by the signal at each frequency, transformed into a digital signal, and output to the data processing unit 40.

Around the same time, the excitation light (ultraviolet light having one or more wavelengths, for example) is illuminated from the light illumination unit 17 to each soil sample in the sample holder 15, and the fluorescence spectrum (spectrum within ultraviolet to visible range, for example) from the soil sample is measured by the light measurement unit 18. The fluorescence spectrum data is temporarily stored in a buffer (not shown) of the data processing unit 40 via the interface unit 19 and input/output interface unit 41. If the obtained fluorescence spectrum is discrete, the smoothing may be performed by finding the moving average with adjacent wavelengths. Also, the data is processed so that the fluorescence spectrum data becomes discrete per specified wavelength intervals.

Then, the estimation unit 44 finds the correlation between the combination of the processed detection signal with one or more fluorescence intensity, of fluorescence spectrum data with respect to arbitrary excitation light, and the quantitative CEC value, and performs the PLS regression analysis. The obtained result is stored in the storage unit 43. When finding the correlation, items for estimating the CEC are extracted based on at least one of the following: one or more items, of the detection signal itself, and amplitude ratio and phase difference between the excitation signal and the detection signal; and either one, or both, of the primary differential value and the secondary differential of the relevant item with respect to frequency. The preparation for analysis has thus been completed.

Similarly, the soil to be analyzed is air-dried, crushed in a mortar, and put into the sample holder 15. Under the control of the control unit 23, the oscillation unit 21 is made to oscillate the signal at each frequency within the specified frequency range (from several kHz to several hundred kHz, for example) while increasing the frequency in stages in arbitrary frequency intervals (several kHz, for example), and to output it to the excitation coil 11. The signal detected by the detection coil 12 is processed by the signal processing unit 22 by the signal at each frequency, transformed into a digital signal, and output to the data processing unit 40.

Around the same time, the excitation light (ultraviolet light having one or more wavelengths, for example) is illuminated from the light illumination unit 17 to each soil sample in the sample holder 15, and the fluorescence spectrum (spectrum within the ultraviolet to visible range, for example) from the soil sample is measured by the light measurement unit 18. The fluorescence spectrum data is temporarily stored in a buffer (not shown) of the data processing unit 40 via the interface unit 19 and input/output interface unit 41. When the obtained fluorescence spectrum is discrete, smoothing may be performed by finding the moving average with adjacent wavelengths. Also, the data is processed so that the fluorescence spectrum data becomes discrete data per specified wavelength intervals.

Then, the estimation unit 44 estimates the CEC of the soil to be analyzed using the data stored in the storage unit 43 based on the processed detection signal output from the signal processing unit 22 and the fluorescence spectrum data output from the light measurement unit 18.

The estimation unit 44 finds the estimated CEC value of the soil to be analyzed based on one or more items, of the processed detection signal itself from the measurement unit 20, and the amplitude ratio and the phase difference between the excitation signal and the detection signal that has (have) correlation with the CEC, and based on items that have correlations with CEC, of the fluorescence spectrum data. The storage unit 43 stores quantitative CEC value of the two or more different types of soil, the detection signal itself processed by the signal processing unit 22 concerning those types of soil, and regression formulae, the average value, etc. concerning each item of the amplitude ratio and the phase difference. In other words, since the detection signal itself processed by the signal processing unit 22 concerning the soil to be analyzed, and the amplitude ratio and the phase difference between the excitation signal and the detection signal are input from the signal processing unit 22, and the fluorescence spectrum data is input from the light measurement unit 18, the CEC value can be estimated by finding how much each item is deviated from the statistical CEC value (average value, for example), finding how much the fluorescence intensity is deviated, and adding the deviations from the statistical CEC value. The estimated CEC value can be found by the method described by referring to FIG. 1 as the intensity itself by the wavelength of the fluorescence data per each excitation light, or as a function of the differential value of the intensity with respect to frequency.

The estimated CEC value=$f(\text{Real}(e_{in}), \text{IMa}(e_{in}), E_{out}/E_{in}, \phi, d''e_{out}/df_n, d''(E_{out}/E_{in})/df_n, d''\phi/df_n, I(\lambda), d''I(\lambda)/df_n)$ Thus, the estimated value is represented as a function of a parameter having a correlation of the following nine parameters: $\text{Real}(e_{in})$, $\text{IMa}(e_{in})$, $E_{out}/E_{in}$, $\phi$, $d''e_{out}/df_n$, $d''(E_{out}/E_{in})/df_n$, $d''\phi/df_n$, $I(\lambda)$, $d''I(\lambda)/df_n$, where $I(\lambda)$ is the fluorescence intensity of the wavelength.

With the soil analyzing device 2 as shown in FIG. 5, since not only the magnetic permeability data is measured by the sensor 10 but also the fluorescence spectrum data is measured using the excitation light, not only CEC but also two or more soil fertility characteristic indexes, such as available nitrogen, available phosphoric acid, total nitrogen, total carbon, and CN ratio, can be found easily.

Example 1

FIG. 6 is an analysis flow chart according to Example 1. As a sample, 10 g of air-dried crushed soil was put in the sample holder 15, and the holder was set (STEP 1-1). Firstly, the detection data itself was obtained using the sensor 10 in 5-kHz intervals within a range from 10 kHz to 100 kHz (STEP 1-2). Also, the excitation light of 392 nm and 375 nm was illuminated to the sample in the sample holder 15, and the 450-nm to 700-nm fluorescence spectrum data was obtained (STEP 1-3).

The data detected by the sensor 10 was handled as follows: The secondary differential value was calculated (STEP 1-4), then the correlation between the quantitative CEC value obtained by the Schollenberger method and the secondary differential value within the 5-kHz to 90-kHz range was found, and the data having high correlation coefficient was used as a sensor-derived explanatory variable. As the result, the following two values were extracted: 30 kHz and 35 kHz (STEP 1-5).

The fluorescence spectrum data was handled as follows: Of the obtained fluorescence spectrum data, five consecutive wavelength data were subjected to moving averaging as smoothing (STEP 1-6). Then, the fluorescence spectra were processed so as to become 5 nm-interval data to maintain 5 nm-interval fluorescence intensity, and the primary differential value was calculated (STEP 1-7). Then, the correlation between CEC value quantified by the Schollenberger method and the primary differential value of the spectrum was found, and the data having high correlation coefficient was used as the fluorescence data-derived explanatory variable. As the result, 6 spectra obtained by 375-nm excitation and 10 spectra obtained by 392-nm excitation were extracted (STEP 1-8)

Then, CEC was estimated by the PLS regression analysis. With the quantitative CEC value used as an objective variable, and the sum total of 18 primary and secondary differential values extracted per each parameter used as explanatory variables, the CEC value was calculated. When creating an analytical curve by the PLS regression analysis, the most appropriate number of latent variables was determined by the cross-validation method.

Figure 7B:
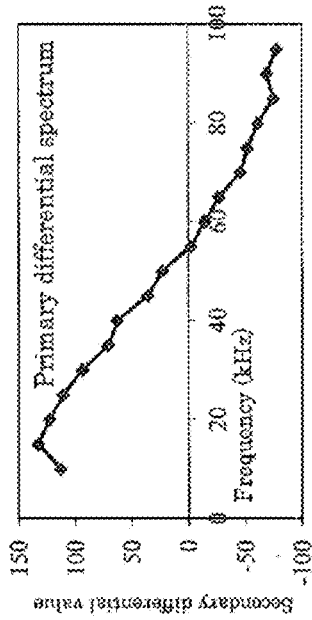
FIGS. 7(a), 7(b), 7(c) and 7(d) are explanatory diagrams of Example 1 showing the refinement of explanatory variables concerning the detection data from the sensor, where
Figure 7D:
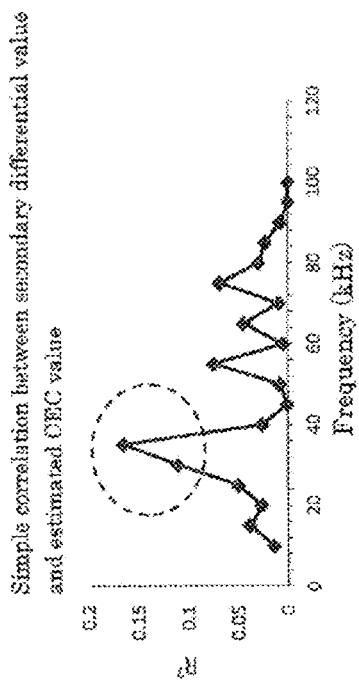
Figure 7A:
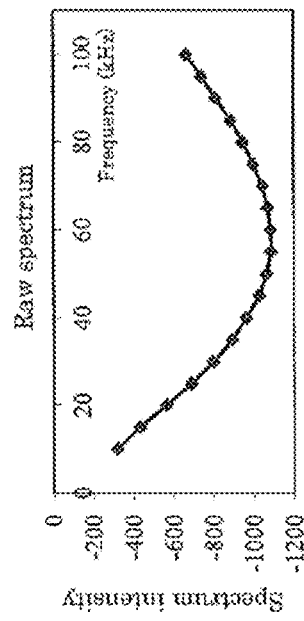
Figure 7C:
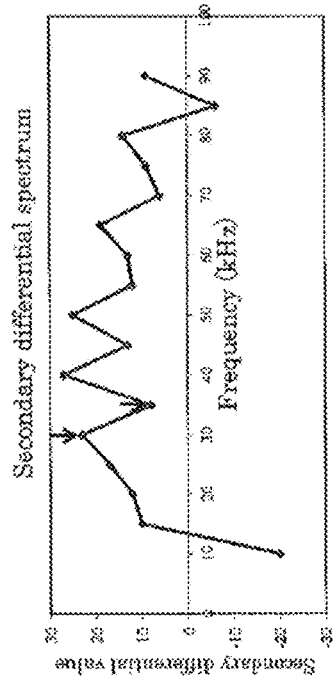

FIGS. 7(a), 7(b), 7(c) and 7(d) are explanatory diagrams showing the refinement of explanatory variables concerning the detection data from the sensor 10. Based on the frequency dependency of the raw spectrum as shown in FIG. 7(a), the primary differential value was calculated as shown in FIG. 7(b), and the secondary differential value was calculated as shown in FIG. 7(c). Then simple correlation between the secondary differential value and quantitative CEC value as shown in FIG. 7(d) was found, and two pieces of data having high correlation coefficient as indicated by arrows in FIG. 7(c) (30-nm and 35-nm data) were extracted. In FIGS. 7(a), 7(b), 7(c) and 7(d), such pieces of data were found based on the frequency dependency of the determination coefficient $R^2$. As shown in FIG. 7(d), the threshold value is determined for the overall variation of the determination coefficient $R^2$, and the specified number of frequencies that exceed the threshold value were selected.

FIGS. 8(a), 8(b), and 8(c) are explanatory charts showing the refinement of explanatory variables concerning the fluorescence spectrum data. As shown in FIG. 8(a), based on the frequency dependency of primary differential value of the fluorescence spectrum by the 392-nm excitation light from the LED, the primary differential value, which is marked by an arrow (↓), is extracted. As shown in FIG. 8(b), based on the frequency dependency of the primary differential value of the fluorescence spectrum by the 375-nm excitation light from the LED, the primary differential values, which are marked by arrows, are extracted. From the relations between the primary differential value and the determination coefficient $R^2$ of the quantitative CEC value as shown in FIG. 8(c), those whose $R^2$ was the threshold value or higher were extracted.

Thus, 16 fluorescence-derived variables and 2 sensor-derived variables, 18 in total, were regarded as explanatory variables.

FIG. 9 shows the result of Example 1, detailing the relation between the estimated CEC value and the quantitative CEC value obtained by refining variables. The relation between the estimated value x and the quantitative value y of CEC was expressed as y=x, and the determination coefficient $R^2$ was 0.85.

Comparative Example 1

FIG. 10 shows, as Comparative Example 1, the relation between the estimated value and the quantitative CEC value obtained when variables were refined using the fluorescence data only. The relation between the estimated value x and the quantitative CEC value y was expressed as $y=x-1\times10^{-12}$, and the determination coefficient $R^2$ was 0.41.

Comparative Example 2

FIG. 11 shows, as Comparative Example 2, the relation between the estimated value and the quantitative CEC value obtained when variables were not refined using fluorescence only. The relation between the estimated value x and the quantitative CEC value y was expressed as $y=x-1\times10^{-12}$, and the determination coefficient $R^2$ was 0.51.

Comparison among FIGS. 9 to 11 reveals that in the case of Example 1, the determination coefficient $R^2$ is close to 1, which means that the estimated CEC value has been calculated highly accurately.

Example 2

FIG. 12 is an analysis flow chart concerning Example 2. As a sample, 10 g of air-dried and crushed soil was put in the sample holder 15, and the holder was set (STEP 2-1). Firstly, the detection data itself and the amplitude ratio data were obtained using the sensor 10 in 5-kHz intervals within a range from 10 kHz to 100 kHz (STEP 2-2). Also, the excitation light of 392 nm and 375 nm was illuminated to the sample in the sample holder 15, and 450-nm to 700-nm fluorescence spectrum data was obtained (STEP 2-3).

Of the data detected by the sensor 10, the obtained detection data and the amplitude ratio data were handled as follows: The secondary differential value of the detection data itself was calculated (STEP 2-4). The amplitude data obtained in 5-kHz intervals was selected (STEP 2-5).

The fluorescence spectrum data was handled as follows: Of the obtained fluorescence spectrum data, five consecutive wavelength data were subjected to moving averaging as smoothing (STEP 2-6). Then, the fluorescence spectra were processed so as to become 5 nm-interval data to maintain 5 nm-interval fluorescence intensity, and the primary differential value was calculated (STEP 2-7).

Then, CEC was estimated by the PLS regression analysis. With the quantitative CEC value used as the objective variable, 52 primary differential value data, 17 secondary differential value data, and 19 amplitude ratio data of the fluorescence spectrum data were used as explanatory variables to estimate CEC value (STEP 2-8).

Explanatory variables in the wavelength range and frequency range where the absolute value of the regression coefficient calculated by this PLS regression analysis was relatively large were extracted. Specifically, 13 spectra obtained by 375-nm excitation, 13 spectra obtained by 392-nm excitation, 8 detection data, and 4 amplitude ratio data were extracted (STEP 2-9).

Then, with the quantitative CEC value used as the objective variable, 38 pieces of data, namely the sum total of primary differential value of fluorescence data extracted in STEP 2-9, secondary differential value of data of real part, and the actual amplitude value, used as explanatory variables, the PLS regression analysis was performed to estimate CEC (STEP 2-10).

FIGS. 13(a) and 13(b) explain parts of the data processing process as shown in the flow chart in FIG. 12. Based on frequency dependency of the amplitude ratio as shown in FIG. 13(a), the frequency dependency of the primary differential value of the amplitude ratio as shown in FIG. 13(b) was found, and furthermore, the frequency dependency of the secondary differential value of the amplitude ratio as shown in FIG. 13(c) was found.

FIG. 14 is a chart showing the result of Example 2. The relation between the estimated CEC value x and the quantitative CEC value y was expressed as $y=x-9\times10^{-14}$, latent variables were 6, coefficient of determination $R^2$ was 0.90, and RMSE was 1.63.

Example 3

FIG. 15 is an analysis flow chart regarding Example 3. As a sample, 10 g of air-dried crushed soil was put in the sample holder 15, and the holder was set (STEP 3-1). Firstly, the detection data itself was obtained using the sensor 10 in 5-kHz intervals within a range from 25 kHz to 200 kHz (STEP 3-2). Also, the excitation light of 392 nm and 375 nm was illuminated to the sample in the sample holder 15, and 450-nm to 700-nm fluorescence spectrum data was obtained (STEP 3-3).

The fluorescence spectrum data was handled as follows: Of the obtained fluorescence spectrum data, five consecutive wavelength data were subjected to moving averaging as smoothing (STEP 3-4). Then, the fluorescence spectra were processed so as to become 5 nm-interval data to maintain 5 nm-interval fluorescence intensity, and the primary differential value was calculated (STEP 3-5).

Each parameter was standardized (STEP 3-6). Specifically, the quantitative CEC value, the detection data itself ranging between 25 kHz and 200 kHz, the amplitude ratio, the phase difference, and the primary differential value data of the fluorescence spectrum data were standardized. Each standardized value was found by dividing the difference between the data and the average value by standard deviation.

With the standardized quantitative CEC value used as an objective variable, and the standardized parameters as explanatory variables, the PLS regression analysis was performed (STEP 3-7). 169 pieces of data in total, i.e. 39 pieces of each data on the detection data itself, the amplitude ratio and the phase difference, 26 on the primary differential data of the fluorescence spectrum data by 375-nm excitation, and 26 on the primary differential data of the fluorescence spectrum data by 392-nm excitation, were used as explanatory variables.

Data, that were calculated by this PLS regression analysis to have relatively large absolute regression coefficient value, were extracted (STEP 3-8). Specifically, 6 pieces of data on the detection data itself, 11 on the amplitude ratio, 9 on the primary differential data of fluorescence spectrum data by 375-nm excitation, and 16 on the primary differential data of fluorescence spectrum data by 392-nm excitation, 42 in total, were used as explanatory variables.

Then, with the standardized quantitative CEC value used as objective variable, and total of 42 pieces of data obtained before standardization in regions extracted in STEP 3-8 (the primary differential value of fluorescence data, the real value of the fluorescence data itself, amplitude ratio) used as explanatory variables, the PLS regression analysis was performed to estimate CEC (STEP 3-9).

Regarding the relation between the estimated CEC value x and the quantitative CEC value y, similar result as shown in FIG. 14 was obtained.

Third Embodiment

A method for estimating the CEC more easily than the first embodiment as well as a method of measuring the soil fertility characteristics other than CEC will hereinafter be described.

As the soil fertility characteristics other than CEC, total carbon (T-C), total nitrogen (T-N), available phosphoric acid (Av-P), total phosphorus (P), iron (Fe), aluminum (Al), and as elements important for plant nutrition, potassium (K), calcium (Ca), magnesium (Mg), etc. can be estimated.

Firstly, in the first embodiment, the estimation unit 34 performs regression analysis and estimates CEC by using one or more items, of the processed detection signal itself output from the measurement unit 20, and the amplitude ratio and the phase difference between the excitation signal and the detection signal, and primary differential value or secondary differential value of the relevant item with respect to frequency, or the primary differential value and the secondary differential value parameters. Whereas in this third embodiment, the real part and imaginary part of the detection signal for the excitation signal only are used as parameters to perform regression analysis and estimation. In other words, the estimated value of the soil fertility characteristics is simplified as shown below.

Estimated soil fertility characteristics=$f$(Real($e_{out}/e_{in}$),Ima($e_{out}/e_{in}$))

In this case, the detection signal for the excitation signal is expressed as the complex number having the real part and the imaginary part. However, the expression by the absolute amplitude and the phase may be allowed, provided that the same complex value is represented.

Similarly to the first embodiment, the estimation unit 34 allows the sensor 10 to apply the alternating magnetic field based on the quantitative value of each of the soil fertility characteristics, performs the PLS regression analysis based on the detection signal processed using the measurement unit 20, and generates data to be stored in the storage unit 33. Note that the methods for measuring the quantitative value of each soil fertility characteristics are as follows:

CEC: Schollenberger method
Total carbon (T-C): Combustion method using C/N coder
Total nitrogen (T-N): Combustion method using C/N coder
Available phosphoric acid (Av-P): Truog method
Fe, Al, Ca, K, Na, Mg: Energy dispersive X-ray fluorescence analysis The estimation unit 34 can analyze the soil fertility characteristics of the soil to be analyzed by using the quantitative value of the soil fertility characteristics including CEC having been found in advance and by following the analysis flow described below.

FIG. 16 is a chart showing the analysis flow regarding the third embodiment. As shown in FIG. 16, the analysis is performed by following the steps described below.

(1) Firstly, the excitation signal is generated in arbitrary frequency intervals, and the alternating magnetic field is applied to the soil to be analyzed (STEP 101).

(2) Then, the complex amplitude ratio to the excitation signal is found from the detection signal obtained from the magnetic field having permeated the soil (STEP 102).

(3) Furthermore, the estimated value of the soil fertility characteristics including CEC is found by using the regression formula based on the regression analysis between the quantitative value of the soil fertility characteristics including CEC of two or more different types of the soil and the complex amplitude ratio of the corresponding detection signal (STEP 103).

In this case, the complex amplitude ratio is defined as the ratio between two signals having different amplitudes and phases represented by the (absolute) amplitude ratio and the phase difference, or by the real part and the imaginary part. Example 4 in the third embodiment will hereinafter be described in detail.

Example 4

As similar to the case of the first embodiment, signals are illuminated to the soil while changing the frequency from 10 kHz to 200 kHz in intervals of 5 kHz, and the magnetic field having permeated the soil was obtained by the signal processing unit 22 via the detection coil 12 of the analyzing device 1. In FIGS. 2(a), 2(b) and 2(c) showing the first embodiment, the PLS correlation coefficient was found by using the primary differential value of the detection signal. Meanwhile, in Example 4, as the simple method, the PLS correlation coefficient was found from the detection signal without performing the primary differentiation of the detection signal but directly from the real part and the imaginary part.

To take an overview of the overall trend, regarding the above quantitative values of each of the soil fertility characteristics, the PLS correlation coefficient of the real part measured instead of the primary differential value as shown in FIGS. 2(a), 2(b) and 2(c), is shown in FIG. 17, and the imaginary part of it is shown in FIG. 18.

As apparent from FIGS. 17 and 18, the frequency exhibiting noticeable correlation varies from element to element. The detailed description will follow by each of the soil fertility characteristics.

(Estimation of Iron)

By using the analyzing device 1 and samples having different iron concentrations, the complex amplitude ratio was found.

FIGS. 19(a) and 19(b) are examples of frequency spectra obtained from the detection signal due to each permeating magnetic field of three samples having different iron contents, with the amplitude of the real part (a) and the imaginary part (b) displayed in intervals of 10 kHz within the range from 10 kHz to 200 kHz. The horizontal axis in FIGS. 19(a) and 19(b) represents frequency. FIGS. 19(a) and 19(b) display the real part and the imaginary part obtained from 3 samples having different iron contents, with the maximum value displayed as S13, median value as S11, and the minimum value as S17. Note that the frequency characteristics unique to the detection circuits are subtracted in advance for display in FIGS. 19(a) and 19(b).

As shown in FIG. 19(a), the amplitude of the real part of the 3 samples having different iron contents increases with the increase in iron contents. Furthermore, as shown in FIG. 19(b), the amplitude of the imaginary part of the 3 samples having different iron contents also increases with the increase in iron content.

Using 30 samples having different iron contents, namely with the number of samples being 30, analysis in step 103 as shown in FIG. 16 was performed.

FIG. 20 is a chart showing the relation between the estimated value x and the quantitative value y of iron in Example 4. As shown in FIG. 20, the number of samples n was 30, latent variables were 4, the correlation was expressed as $y=x-4\times10^{-13}$, the determination coefficient $R^2$ was 0.9643, and RMSE was 0.23 The following soil fertility characteristics including CEC were also analyzed in the same way as the estimation of iron.

(Estimation of Total Carbon)

FIG. 21 is a chart showing the relation of the estimated value x and the quantitative value y of total carbon in Example 4. As shown in this figure, the number of samples n was 30, latent variables were 8, the correlation was expressed as $y=x-6\times10^{-14}$, the determination coefficient $R^2$ was 0.9984, and RMSE was 0.08.

(Estimation of Total Nitrogen)

FIG. 22 is a chart showing the relation between the estimated value x and the quantitative value y of total nitrogen in Example 4. As shown in this figure, the number of samples n was 30, latent variables were 6, the correlation was expressed as $y=x-2\times10^{-13}$, the determination coefficient $R^2$ was 0.9858, and RMSE was 0.02.

(Estimation of CEC)

FIG. 23 is a chart showing the relation between the estimated value x and the quantitative value y of CEC in Example 4. As shown in FIG. 23, the number of samples n was 30, latent variables were 5, the correlation was expressed as $y=x$, the determination coefficient $R^2$ was 0.9751, and RMSE was 0.80.

(Estimation of Available Phosphoric Acid)

FIG. 24 is a chart showing the relation between the estimated value x and the quantitative value y of available phosphoric acid in Example 4. As shown in FIG. 24, the number of samples n was 30, latent variables were 12, the correlation was expressed as $y=x+1\times10^{-13}$, the determination coefficient $R^2$ was 1, and RMSE was 0.21.

(Estimation of Total Phosphorus)

FIG. 25 is a chart showing the relation between the estimated value x and the quantitative value y of total phosphorus in Example 4. As shown in FIG. 25, the number of samples n was 30, latent variables were 14, the correlation was expressed as $y=x-6\times10^{-14}$, the determination coefficient $R^2$ was 1, and RMSE was $6.9\times10^{-5}$.

(Estimation of Potassium)

FIG. 26 is a chart showing the relation between the estimated value x and the quantitative value y of potassium in Example 4. As shown in FIG. 26, the number of samples n was 30, latent variables were 4, the correlation was expressed as $y=x-4\times10^{-13}$, the determination coefficient $R^2$ was 0.898, and RMSE was 0.06.

(Estimation of Calcium)

FIG. 27 is a chart showing the relation between the estimated value x and the quantitative value y of calcium in Example 4. As shown in this figure, the number of samples n was 30, latent variables were 3, the correlation was expressed as $y=x-7\times10^{-14}$, the determination coefficient $R^2$ was 0.742, and RMSE was 0.46.

(Estimation of Magnesium)

FIG. 28 is a chart showing the relation between the estimated value x and the quantitative value y of magnesium in Example 4. As shown in FIG. 28, the number of samples n was 30, latent variables were 2, the correlation was expressed as $y=x+4\times10^{-13}$, the determination coefficient $R^2$ was 0.196, and RMSE was 0.10.

(Estimation of Aluminum)

FIG. 29 is a chart showing the relation between the estimated value x and the quantitative value y of aluminum in Example 4. As shown in the figure, the number of samples n was 30, latent variables were 3, the correlation was expressed as $y=x-10^{-12}$, the determination coefficient $R^2$ was 0.8067, and RMSE was 0.62.

(Estimation of sum total of Fe, Al, Ca, K, Na, and Mg)

FIG. 30 is a chart showing the relation between the estimated value x and the quantitative value y of sum total of Fe, Al, Ca, K, Na, and Mg in Example 4. These elements can become cations. Although Al ions have toxicity on plants, Al is an essential constituent element of crystalline clay minerals. As shown in FIG. 30, the number of samples n was 30, latent variables were 3, the correlation was expressed as $y=x+8\times10^{-13}$, the determination coefficient $R^2$ was 0.9496, and RMSE was 0.52.

From the above Example 4, it was found that by applying magnetic field to the soil to be analyzed and using the sensor 10 for detection, the data including magnetic permeability of the soil can be obtained, and as soil fertility characteristics including CEC, the value of total carbon, total nitrogen, available phosphoric acid, total phosphorus, iron, aluminum, potassium, calcium, magnesium, and the sum of elements that can become cations (Fe, Al, Ca, K, Na, Mg) can be estimated highly accurately.

As described above, according to the embodiment of the present invention, by applying the magnetic field to the soil to be analyzed and by using the detection coil 12 for detection, the data including magnetic permeability of the soil can be obtained, and the value of soil fertility characteristics including CEC can be estimated highly accurately. The CEC value is an index that indicates how many cations of bases (such as Ca, Mg, K, Na, ammonium, and H) can be absorbed by electrically negative soil at the maximum, the value indicating the capacity of storing nutrient having fertilizer effect as well as buffer power. Since the indexes regarding the soil fertility characteristics including CEC can be found easily and highly accurately, the soil can be managed more easily, resulting in improvement in productivity of agricultural products.

The embodiments of the present invention, the methods of data processing described in examples, in particular, are just examples, and may be changed as required based on contrivance in general programming methods. For example, the differential calculation can be substituted by difference calculation.

In the embodiments of the present invention, since the detection signal affected by the magnetic permeability, etc. of the soil is measured by applying the magnetic field to the soil, even the indexes for the soil fertility characteristics including CEC of even cloudy soil can be analyzed. By using the fluorescence data in conjunction with the detection data by the sensor 10, the analysis of soil can be complemented.

REFERENCE SIGNS LIST

1, 2: Soil analyzing device
10: Sensor
11: Excitation coil
12: Detection coil
13: Magnetic path forming part 14: Sensor holder
15: Sample holder
16: Dark box
17: Light illumination unit
18: Light measurement unit
19: Interface unit
20: Measurement unit
21: Oscillation unit
22: Signal processing unit
23: Control unit
30, 40: Data processing unit
31, 41: Input/output (I/O) interface unit
32, 42: Storage device
33, 43: Storage unit
34, 44: Estimation unit
45: Measurement control unit

What is claimed is:

1. A soil analyzing device, comprising:
a sensor having a coil;
a measurement unit that generates an excitation signal to be input to the coil per frequency in order to apply an alternating magnetic field to the soil to be analyzed, and processes a detection signal output from the coil by applying the alternating magnetic field to the soil to be analyzed;
a storage unit that stores data concerning the correlation between a quantitative value of the soil fertility characteristics including CEC of two or more types of the soil having different components and an estimated value of the soil fertility characteristics including CEC found from the processed detection signal measured by using the sensor and the measurement unit; and
an estimation unit that estimates the soil fertility characteristics including CEC of the soil to be analyzed based on the detection signal generated by allowing the sensor to apply the alternating magnetic field to the soil to be analyzed and processed using the measurement unit and by using the data stored in the storage unit, wherein the estimation unit extracts items for estimating the soil fertility characteristics including CEC of the soil to be analyzed based on at least one of the following: one or more items, of the processed detection signal itself output from the measurement unit, and amplitude ratio and the phase difference between the excitation signal and the detection signal; and either one, or both, of a primary differential value and a secondary differential value of the relevant item with respect to frequency.

2. The soil analyzing device as set forth in claim 1, wherein the estimation unit estimates the soil fertility characteristics including CEC of the soil to be analyzed based on one or more items, of the processed detection signal itself output from the measurement unit, and the amplitude ratio and the phase difference between the excitation signal and the detection signal, that has (have) the correlation with the soil fertility characteristics including CEC of the soil to be analyzed.

3. The soil analyzing device as set forth in claim 1, wherein the estimation unit finds a complex amplitude ratio with respect to the excitation signal based on the detection signal, and estimates the soil fertility characteristics by using a regression formula based on the regression analysis between the quantitative value of the soil fertility characteristics of different types of the soil stored in the storage unit and the complex amplitude ratio of the corresponding detection signal.

4. The soil analyzing device as set forth in claim 3, wherein the complex amplitude ratio is represented by the absolute amplitude ratio and the phase difference, or by the real part and the imaginary part, and the regression formula has the absolute amplitude ratio and the phase difference, or the real part and the imaginary part, as independent variables respectively.

5. The soil analyzing device as set forth in claim 1, wherein the estimation unit performs the partial least squares (PLS) regression analysis of two or more types of the soil having different components based on the quantitative value of the soil fertility characteristics including CEC and the detection signal obtained by allowing the sensor to apply the alternating magnetic field and processed by using the measurement unit, and generates the data to be stored in the storage unit.

6. A soil analyzing device, comprising:
a sensor having a coil;
a measurement unit that generates an excitation signal to be input to the coil in order to apply an alternating magnetic field to the soil to be analyzed and processes a detection signal output from the coil by applying the alternating magnetic field to the soil to be analyzed;
a light illumination unit that illuminates an excitation light to the soil to be analyzed;
a light measurement unit that measures a fluorescence from the soil to be analyzed, following the illumination of light from the light illumination unit;
a storage unit that stores data concerning correlation between a quantitative value of the soil fertility characteristics including CEC of two or more types of the soil having different components and an estimated value of the soil fertility characteristics including CEC found based on the processed detection signal measured using the sensor and the measurement unit, and the fluorescence spectrum data measured using the light illumination unit and the light measurement unit; and
an estimation unit that estimates the soil fertility characteristics including CEC of the soil to be analyzed based on the detection signal generated by allowing the sensor to apply the alternating magnetic field and processed using the measurement unit, and the fluorescence spectrum data obtained by allowing the light illumination unit to illuminates the excitation light and measured by the measurement unit, and by using the data stored in the storage unit, wherein items for estimating the soil fertility characteristics including CEC of the soil to be analyzed are extracted based on at least on of the following: one or more items, of the processed detection signal itself output from the measurement unit, and the amplitude ratio and the phase difference between the excitation signal and the detection signal; and either one, or both, of the primary differential value and the secondary differential value of the relevant item with respect to frequency, and wherein
the fluorescence spectrum data for estimating the soil fertility characteristics including CEC of the soil to be analyzed is extracted based on either one, or both, of the primary differential value and the secondary differential value, with respect to frequency, of the fluorescence spectrum data output from the light measurement unit.

7. The soil analyzing device as set forth in claim 6, wherein the estimation unit estimates the soil fertility characteristics of the soil to be analyzed based on one or more items, of the processed detection signal itself output from the measurement unit, and the amplitude ratio and the phase difference between the excitation signal and the detection signal, that has (have) the correlation items with the soil fertility characteristics including CEC of the soil to be analyzed, and based on the data having the correlation with the soil fertility characteristics including CEC of the soil to be analyzed, of the fluorescence spectrum data measured by the light measurement unit.

8. The soil analyzing device as set forth in claim 6, wherein the estimation unit performs the PLS regression analysis of two or more types of the soil having different components based on the quantitative value of the soil fertility characteristics including CEC, the detection signal obtained by allowing the sensor to apply the alternating magnetic field and processed using the measurement signal, and the fluorescence spectrum data obtained by allowing the light illumination unit to illuminate the excitation light and measured by the measurement unit, and generates the data to be stored in the storage unit.

9. A soil analyzing method, comprising steps of:
generating an excitation signal by arbitrary frequencies and applying an alternating magnetic field to the soil to be analyzed;
finding a complex amplitude ratio to the excitation signal from a detection signal obtained from the magnetic field having permeated the soil; and
estimating the soil fertility characteristics including CEC by a regression formula based on regression analysis between a quantitative value of the soil fertility characteristics including CEC of two or more different types of the soil and the complex amplitude ratio of a corresponding detection signal, wherein the complex amplitude ratio is represented by the absolute amplitude ratio and the phase difference, or the real part and the imaginary part, and the regression formula has the absolute amplitude ratio and the phase difference, or the real part and the imaginary part, as independent variables respectively.

10. The soil analyzing method as set forth in claim 9, wherein the regression formula is generated by performing the PLS regression analysis based on the quantitative value of the soil fertility characteristics including CEC of two or more types of the soil having different components and the detection signal obtained from the magnetic field having permeated the soil.

11. The soil analyzing method as set forth in claim 9, wherein the regression formula is generated by performing the PLS regression analysis based on the quantitative value of the soil fertility characteristics including CEC of two or more types of the soil having different components and the detection signal obtained from the magnetic field having permeated the soil.

* * * * *